(12) United States Patent
Chatelier et al.

(10) Patent No.: US 9,157,110 B2
(45) Date of Patent: Oct. 13, 2015

(54) SYSTEMS AND METHODS OF DISCRIMINATING CONTROL SOLUTION FROM A PHYSIOLOGICAL SAMPLE

(75) Inventors: Ronald C. Chatelier, Bayswater (AU); Alastair M. Hodges, Blackburn South (AU)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 13/611,703

(22) Filed: Sep. 12, 2012

(65) Prior Publication Data

US 2013/0001103 A1    Jan. 3, 2013

Related U.S. Application Data

(62) Division of application No. 12/211,484, filed on Sep. 16, 2008.

(60) Provisional application No. 60/976,083, filed on Sep. 28, 2007.

(51) Int. Cl.
*G01N 27/28* (2006.01)
*C12Q 1/00* (2006.01)
*G01N 33/543* (2006.01)
*G01N 33/96* (2006.01)
*G01N 27/327* (2006.01)

(52) U.S. Cl.
CPC .......... *C12Q 1/001* (2013.01); *G01N 27/3274* (2013.01); *G01N 33/5438* (2013.01); *G01N 33/96* (2013.01)

(58) Field of Classification Search
CPC ............... C12Q 1/001; G01N 27/3274; G01N 33/5438; G01N 33/96
USPC ......................................... 205/775
See application file for complete search history.

(56) References Cited

U.S. PATENT DOCUMENTS

| 3,648,160 A | 3/1972 | Beaver |
| 4,088,448 A | 5/1978 | Lilja et al. |

(Continued)

FOREIGN PATENT DOCUMENTS

| AU | 3104293 A | 7/1993 |
| AU | 5487394 | 8/1994 |

(Continued)

OTHER PUBLICATIONS

CA Office Action for 2,748,433; dated Aug. 1, 2013; 3 pages.

(Continued)

*Primary Examiner* — Alexander Noguerola
*Assistant Examiner* — Steven Rosenwald
(74) *Attorney, Agent, or Firm* — Barclay Damon, LLP

(57) ABSTRACT

Methods for distinguishing between an aqueous non-blood sample (e.g., a control solution) and a blood sample. In one aspect, the methods include using a test strip in which multiple current transients are measured by a meter electrically connected to an electrochemical test strip. The current transients are used to determine if a sample is a blood sample or an aqueous non-blood sample based on at least two characteristics (e.g., amount of interferent present and reaction kinetics). The method can also include calculating a discrimination criteria based upon at least two characteristics. Various aspects of a system for distinguishing between blood samples and an aqueous non-blood sample are also provided herein.

5 Claims, 12 Drawing Sheets

(56) References Cited

U.S. PATENT DOCUMENTS

| | | |
|---|---|---|
| 4,224,125 A | 9/1980 | Nakamura et al. |
| 4,233,029 A | 11/1980 | Columbus |
| 4,250,257 A | 2/1981 | Lee et al. |
| 4,254,083 A | 3/1981 | Columbus |
| 4,259,165 A | 3/1981 | Miyake et al. |
| 4,301,412 A | 11/1981 | Hill et al. |
| 4,301,414 A | 11/1981 | Hill et al. |
| 4,303,887 A | 12/1981 | Hill et al. |
| 4,307,188 A | 12/1981 | White |
| 4,374,013 A | 2/1983 | Enfors et al. |
| 4,404,066 A | 9/1983 | Johnson |
| 4,431,004 A | 2/1984 | Bessman et al. |
| 4,436,812 A | 3/1984 | Endoh et al. |
| 4,508,613 A | 4/1985 | Busta et al. |
| 4,517,287 A | 5/1985 | Scheibe et al. |
| 4,517,291 A | 5/1985 | Seago |
| 4,533,440 A | 8/1985 | Kim |
| 4,545,382 A | 10/1985 | Higgins et al. |
| 4,547,735 A | 10/1985 | Kiesewetter |
| 4,552,840 A | 11/1985 | Riffer |
| 4,629,563 A | 12/1986 | Wrasidlo |
| 4,654,197 A | 3/1987 | Lilja et al. |
| 4,664,119 A | 5/1987 | Bessman et al. |
| 4,686,479 A | 8/1987 | Young |
| 4,711,245 A | 12/1987 | Higgins et al. |
| 4,774,039 A | 9/1988 | Wrasidlo |
| 4,790,925 A | 12/1988 | Miller et al. |
| 4,900,424 A | 2/1990 | Birth et al. |
| 4,919,770 A | 4/1990 | Preidel et al. |
| 4,963,815 A | 10/1990 | Hafeman |
| 5,059,908 A | 10/1991 | Mina |
| 5,064,516 A | 11/1991 | Rupich |
| 5,089,320 A | 2/1992 | Straus et al. |
| 5,108,564 A | 4/1992 | Szuminsky et al. |
| 5,120,420 A | 6/1992 | Nankai et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,151,166 A | 9/1992 | Harral et al. |
| 5,171,689 A | 12/1992 | Kawaguri et al. |
| 5,192,415 A | 3/1993 | Yoshioka et al. |
| 5,229,282 A | 7/1993 | Yoshioka et al. |
| 5,243,516 A | 9/1993 | White |
| 5,272,060 A | 12/1993 | Hamamoto et al. |
| 5,272,087 A | 12/1993 | El Murr et al. |
| 5,282,950 A | 2/1994 | Dietze et al. |
| 5,312,590 A | 5/1994 | Gunasingham et al. |
| 5,320,732 A | 6/1994 | Nankai et al. |
| 5,352,351 A | 10/1994 | White et al. |
| 5,382,346 A | 1/1995 | Uenoyama et al. |
| 5,384,028 A | 1/1995 | Ito et al. |
| 5,385,846 A | 1/1995 | Kuhn et al. |
| 5,388,163 A | 2/1995 | Elko et al. |
| 5,393,399 A | 2/1995 | Van den Berg et al. |
| 5,395,504 A | 3/1995 | Saurer et al. |
| 5,405,511 A | 4/1995 | White et al. |
| 5,413,690 A | 5/1995 | Kost et al. |
| 5,437,999 A | 8/1995 | Diebold et al. |
| 5,469,369 A | 11/1995 | Rose-Pehrsson et al. |
| 5,508,171 A | 4/1996 | Walling et al. |
| 5,508,203 A | 4/1996 | Fuller |
| 5,509,410 A | 4/1996 | Hill et al. |
| 5,520,787 A | 5/1996 | Hanagan et al. |
| 5,527,446 A | 6/1996 | Kosek et al. |
| 5,567,302 A | 10/1996 | Song et al. |
| 5,611,908 A | 3/1997 | Matthiessen et al. |
| 5,620,579 A | 4/1997 | Genshaw et al. |
| 5,628,890 A | 5/1997 | Carter et al. |
| 5,642,734 A | 7/1997 | Ruben |
| 5,645,709 A | 7/1997 | Birch et al. |
| 5,653,863 A | 8/1997 | Genshaw et al. |
| 5,660,791 A | 8/1997 | Brenneman et al. |
| 5,723,284 A | 3/1998 | Ye |
| 5,762,770 A | 6/1998 | Pritchard et al. |
| 5,849,174 A | 12/1998 | Sanghera et al. |
| 5,869,971 A | 2/1999 | Sherman |
| 5,909,114 A | 6/1999 | Uchiyama et al. |
| 5,942,102 A | 8/1999 | Hodges et al. |
| 5,997,817 A | 12/1999 | Crismore et al. |
| 6,058,934 A | 5/2000 | Sullivan |
| 6,071,391 A | 6/2000 | Gotoh et al. |
| 6,153,069 A | 11/2000 | Pottgen et al. |
| 6,179,979 B1 | 1/2001 | Hodges et al. |
| 6,193,873 B1 | 2/2001 | Ohara et al. |
| 6,251,260 B1 | 6/2001 | Heller et al. |
| 6,284,125 B1 | 9/2001 | Hodges et al. |
| 6,287,451 B1 | 9/2001 | Winarta et al. |
| 6,379,513 B1 | 4/2002 | Chambers et al. |
| 6,391,645 B1 | 5/2002 | Huang et al. |
| 6,413,410 B1 | 7/2002 | Hodges et al. |
| 6,461,496 B1 | 10/2002 | Feldman et al. |
| 6,475,372 B1 | 11/2002 | Ohara et al. |
| 6,503,381 B1 | 1/2003 | Gotoh et al. |
| 6,576,117 B1 | 6/2003 | Iketaki et al. |
| 6,595,919 B2 | 7/2003 | Berner et al. |
| 6,645,368 B1 | 11/2003 | Beaty et al. |
| 6,676,995 B2 | 1/2004 | Dick et al. |
| 6,730,200 B1 | 5/2004 | Stewart et al. |
| 6,749,887 B1 | 6/2004 | Dick et al. |
| 6,816,537 B2 | 11/2004 | Liess |
| 6,818,180 B2 | 11/2004 | Douglas et al. |
| 6,824,670 B2 | 11/2004 | Tokunaga et al. |
| 6,830,934 B1 | 12/2004 | Harding et al. |
| 6,863,801 B2 | 3/2005 | Hodges et al. |
| 6,869,411 B2 | 3/2005 | Langley et al. |
| 6,936,146 B2 | 8/2005 | Ryu et al. |
| 6,942,770 B2 | 9/2005 | Cai et al. |
| 7,008,525 B2 | 3/2006 | Morita et al. |
| 7,018,843 B2 | 3/2006 | Heller |
| 7,083,712 B2 | 8/2006 | Morita et al. |
| 7,122,111 B2 | 10/2006 | Tokunaga et al. |
| 7,132,041 B2 | 11/2006 | Deng et al. |
| 7,160,251 B2 | 1/2007 | Neel et al. |
| 7,201,042 B2 | 4/2007 | Yamaoka et al. |
| 7,338,639 B2 | 3/2008 | Burke et al. |
| 7,390,667 B2 | 6/2008 | Burke |
| 7,407,811 B2 | 8/2008 | Burke |
| 7,452,457 B2 | 11/2008 | Burke |
| 7,488,601 B2 | 2/2009 | Burke |
| 7,494,816 B2 | 2/2009 | Burke |
| 7,504,020 B2 | 3/2009 | Tokunaga et al. |
| 7,597,793 B2 | 10/2009 | Burke |
| 7,604,721 B2 | 10/2009 | Groll |
| 7,645,373 B2 | 1/2010 | Groll |
| 7,645,421 B2 | 1/2010 | Groll |
| 7,718,439 B2 | 5/2010 | Groll |
| 7,727,467 B2 | 6/2010 | Burke |
| 7,749,371 B2 | 7/2010 | Guo et al. |
| 7,749,437 B2 | 7/2010 | Mosoiu |
| 7,829,023 B2 | 11/2010 | Burke |
| 7,879,618 B2 | 2/2011 | Mosoiu |
| 7,892,849 B2 | 2/2011 | Burke |
| 7,923,258 B2 | 4/2011 | Heller |
| 7,927,882 B2 | 4/2011 | Heller |
| 7,955,492 B2 | 6/2011 | Fujiwara |
| 7,972,861 B2 | 7/2011 | Deng |
| 7,977,112 B2 | 7/2011 | Burke |
| 7,981,363 B2 | 7/2011 | Burke |
| 2002/0139692 A1 | 10/2002 | Tokunaga et al. |
| 2003/0036202 A1 | 2/2003 | Teodorcyzk et al. |
| 2003/0098233 A1 | 5/2003 | Kermani et al. |
| 2003/0109798 A1 | 6/2003 | Kermani |
| 2004/0005716 A9 | 1/2004 | Beaty |
| 2004/0079652 A1 | 4/2004 | Vreeke et al. |
| 2004/0120848 A1 | 6/2004 | Teodorczyk |
| 2004/0154932 A1 | 8/2004 | Deng et al. |
| 2004/0182703 A1 | 9/2004 | Bell et al. |
| 2004/0219624 A1 | 11/2004 | Teodorczyk et al. |
| 2004/0235178 A1 | 11/2004 | Tokunaga et al. |
| 2004/0256248 A1 | 12/2004 | Burke et al. |
| 2005/0036906 A1 | 2/2005 | Nakahara |
| 2005/0045476 A1 | 3/2005 | Neel et al. |
| 2005/0153457 A1 | 7/2005 | Patel et al. |

(56) References Cited

U.S. PATENT DOCUMENTS

| | | | |
|---|---|---|---|
| 2005/0247562 A1* | 11/2005 | Tokunaga et al. | 204/450 |
| 2005/0284758 A1 | 12/2005 | Funke | |
| 2006/0108236 A1 | 5/2006 | Kasielke et al. | |
| 2006/0231418 A1 | 10/2006 | Harding et al. | |
| 2006/0231421 A1 | 10/2006 | Diamond et al. | |
| 2006/0231423 A1 | 10/2006 | Harding et al. | |
| 2006/0231425 A1 | 10/2006 | Harding et al. | |
| 2007/0000777 A1 | 1/2007 | Ho et al. | |
| 2007/0017824 A1 | 1/2007 | Rippeth et al. | |
| 2007/0074977 A1 | 4/2007 | Guo et al. | |
| 2007/0102292 A1 | 5/2007 | Dreibholz et al. | |
| 2007/0227912 A1 | 10/2007 | Chatelier et al. | |
| 2007/0235346 A1 | 10/2007 | Popovich et al. | |
| 2007/0235347 A1* | 10/2007 | Chatelier et al. | 205/792 |
| 2007/0256943 A1 | 11/2007 | Popovich | |
| 2008/0083618 A1 | 4/2008 | Neel et al. | |
| 2009/0014339 A1 | 1/2009 | Beer et al. | 205/777.5 |
| 2009/0084687 A1* | 4/2009 | Chatelier et al. | 205/792 |
| 2009/0099787 A1 | 4/2009 | Carpenter | |
| 2009/0184004 A1 | 7/2009 | Chatelier et al. | |
| 2009/0301899 A1 | 12/2009 | Hodges et al. | |
| 2010/0089775 A1 | 4/2010 | Chen | |
| 2010/0170807 A1 | 7/2010 | Diebold | |
| 2010/0206749 A1 | 8/2010 | Choi | |
| 2010/0276303 A1 | 11/2010 | Fujiwara | |
| 2011/0011752 A1 | 1/2011 | Chatelier et al. | |
| 2011/0297554 A1 | 12/2011 | Wu | |
| 2011/0301857 A1 | 12/2011 | Huang | |

FOREIGN PATENT DOCUMENTS

| | | | |
|---|---|---|---|
| AU | 2007201377 | | 8/2009 |
| AU | 2009200097 | | 1/2011 |
| AU | 2009202200 | | 1/2011 |
| CA | 2748433 | | 9/2007 |
| CA | 2582643 | | 10/2011 |
| CN | 1338049 | A | 2/2002 |
| CN | 1692277 | A | 11/2005 |
| DE | 3103464 | | 8/1982 |
| EP | 0171375 | A1 | 2/1986 |
| EP | 0172969 | A2 | 3/1986 |
| EP | 0251915 | | 1/1988 |
| EP | 0255291 | A1 | 2/1988 |
| EP | 0266204 | | 5/1988 |
| EP | 0278647 | | 8/1988 |
| EP | 0278647 | A2 | 8/1988 |
| EP | 0290770 | A2 | 11/1988 |
| EP | 0299779 | | 1/1989 |
| EP | 0351516 | | 1/1990 |
| EP | 0351891 | A2 | 1/1990 |
| EP | 0351892 | A2 | 1/1990 |
| EP | 0359831 | A1 | 3/1990 |
| EP | 0400918 | | 12/1990 |
| EP | 0418404 | | 3/1991 |
| EP | 0451981 | A2 | 10/1991 |
| EP | 0560336 | A1 | 9/1993 |
| EP | 0800086 | A1 | 10/1997 |
| EP | 1 042 667 | A1 | 10/2000 |
| EP | 1 156 324 | A1 | 11/2001 |
| EP | 1156324 | A1 | 11/2001 |
| EP | 1172649 | A1 | 1/2002 |
| EP | 1256798 | A1 * | 11/2002 ............... C12Q 1/00 |
| EP | 1 281 960 | A2 | 2/2003 |
| EP | 1281960 | A2 | 2/2003 |
| EP | 1 394 545 | A1 | 3/2004 |
| EP | 1447452 | A1 | 8/2004 |
| EP | 1557662 | A1 | 7/2005 |
| EP | 1 775 587 | A2 | 4/2007 |
| EP | 1 840 219 | A1 | 10/2007 |
| EP | 1839571 | A1 | 10/2007 |
| EP | 1840219 | A1 | 10/2007 |
| EP | 2098857 | | 12/2009 |
| EP | 2267149 | | 12/2010 |
| EP | 2076168 | | 1/2012 |
| EP | 2 482 069 | A1 | 8/2012 |
| GB | 2020424 | | 11/1979 |
| GB | 2154735 | | 9/1985 |
| GB | 2201248 | | 8/1988 |
| GB | 2235050 | | 2/1991 |
| JP | 3099254 | | 4/1991 |
| JP | 3167464 | | 7/1991 |
| JP | 4066112 | | 3/1992 |
| JP | 4343065 | A | 11/1992 |
| JP | 5002007 | A | 1/1993 |
| JP | 6222874 | | 8/1994 |
| JP | 11230934 | A | 8/1999 |
| JP | 2001-066274 | A | 3/2001 |
| JP | 200166274 | | 3/2001 |
| JP | 2001153839 | A | 6/2001 |
| JP | 2003114214 | A | 4/2003 |
| JP | 2003-185615 | | 7/2003 |
| JP | 2003521708 | A | 7/2003 |
| JP | 2003240747 | | 8/2003 |
| JP | 2003-262604 | | 9/2003 |
| JP | 2004245836 | A | 9/2004 |
| JP | 2005147990 | A | 6/2005 |
| JP | 2007087710 | | 4/2007 |
| JP | 2007108171 | A | 4/2007 |
| JP | 2007133985 | | 5/2007 |
| JP | 2007522449 | | 8/2007 |
| JP | 2007225619 | | 9/2007 |
| JP | 2007248281 | | 9/2007 |
| JP | 2007271623 | | 10/2007 |
| JP | 2007531877 | | 11/2007 |
| JP | 2009528540 | | 8/2009 |
| JP | 2009-536744 | A | 10/2009 |
| SU | 1351627 | | 11/1987 |
| WO | WO-8908713 | A1 | 9/1989 |
| WO | WO-9215701 | A1 | 9/1992 |
| WO | WO-9402842 | A1 | 2/1994 |
| WO | WO-9516198 | A1 | 6/1995 |
| WO | WO-9700441 | A1 | 1/1997 |
| WO | WO-9718465 | A1 | 5/1997 |
| WO | WO-0020626 | A1 | 4/2000 |
| WO | 01/40787 | A1 | 6/2001 |
| WO | WO-0157510 | A2 | 8/2001 |
| WO | 2004040286 | A1 | 5/2004 |
| WO | WO2004113913 | | 12/2004 |
| WO | WO 2005/008231 | A1 | 1/2005 |
| WO | WO2005066355 | | 7/2005 |
| WO | 2005098424 | A1 | 10/2005 |
| WO | WO 2006/109280 | A2 | 10/2006 |
| WO | WO 2006/110504 | A1 | 10/2006 |
| WO | WO2006109277 | | 10/2006 |
| WO | WO-2006110504 | A1 | 10/2006 |
| WO | 2007/133985 | A2 | 11/2007 |
| WO | 2007130907 | A2 | 11/2007 |
| WO | WO 2008/004565 | A1 | 1/2008 |

OTHER PUBLICATIONS

AU Examination Report for 2012201914; dated Sep. 6, 2013; 2 pgs.
AU Examination Report for 2012201915; dated Sep. 6, 2013; 2 pgs.
Chinese Office Action and Search Report for CN 200810175601.0; dated Mar. 20, 2013; 7 pages.
EP Examination Report for EP 09 250 133.7; dated May 16, 2013; 4 pages.
EP Examination Report for EP 12 164 561.8; dated May 2, 2013; 2 pages.
AU Examination Report for 2012201912; dated Jan. 11, 2013; 4 pages.
AU Examination Report for 2012201916; dated Jan. 24, 2013; 4 pages.
AU Examination Report for 2009227823; dated Feb. 18, 2013; 3 pages.
JP Office Action for 2012-261693; dated Feb. 5, 2013; 2 pages.
EP report for 07251388 dated Jun. 5, 2012.
EP report for 08253148 dated Jun. 4, 2012.
EP report for 10178905 dated Jun. 8, 2012.
EP report for 10178982 dated Jun. 5, 2012.
Wikipedia: Hematocrit; Retrieved on May 24, 2012 (3 pages).

(56) References Cited

OTHER PUBLICATIONS

EP report for 12164561 dated Jul. 4, 2012.
Schmidt, "New Principles of amperometric enzyme electrodes . . ." Sensors and Actuators B; vol. 13, No. 1-3, May 1, 1993.
EP report for 12173292 dated Sep. 12, 2012.
EP report for 12173297 dated Sep. 14, 2012.
EP report or 12173284 dated Sep. 7, 2012.
JP report for 2012076986 dated Sep. 4, 2012.
Cha, Kichul, et al., An electronic method for rapid measurement of haematocrit in blood samples; Physiol Meas, 1994.
CN report for 200910134602 dated Aug. 17, 2012.
JP report for 2009137856 dated Jul. 31, 2012.
EP report for 09251507.1 dated Sep. 13, 2012.
AU report for 2009227823 dated Nov. 1, 2012.
SG report or 200900312-0 dated Oct. 11, 2012.
Wikipedia: "Hematocrit"; http://en.wikipedia.org/w/index.php?title=Hematocrit&printable=yes; Retrieved on May 24, 2012; 3 pages.
European Search Report for EP Application No. 08 253 148.4; mailed Jun. 4, 2012; 3 pages.
European Search Report for EP Application No. 07 251 388.0; mailed Jun. 5, 2012; 3 pages.
European Search Report for EP Application No. 10 178 982.4; mailed Jun. 5, 2012; 2 pages.
European Search Report for EP Application No. 10 178 905.5; mailed Jun. 8, 2012; 4 pages.
Chinese Office Action issued Nov. 22, 2011 for Application No. 200910134602.5 (15 Pages).
Japanese Office Action issued Nov. 29, 2011 for Application No. 2009-006871 (3 Pages).
Japanese Office Action issued Jan. 10, 2012 tor Application No. 2011-123761 (3 Pages).
Numerical Recipes: The Art of Scientific Computing, Third Editon. William H. Press et al., Cambridge University Press, Published 2007.
European Extended Search Report for Application No. EP 09250133, dated Nov. 30, 2009, 10 pages.
European Extended Search Report for Application No. EP 09251507, dated Sep. 14, 2011, 11 pages.
European Extended Search Report for Application No. 07251388.0, dated Jul. 9, 2007, 6 pages.
Canadian Examiner's Requisition for Application No. 2648625, dated Apr. 11, 2011, 3 pages.
Japanese Office Action for Application No. JP 2007-087710, mailed Aug. 9, 2011, 2 pages.
European Search Report, Application No. EP 09251507, mailed May 11, 2011, 5 pages.
Australian Examiner's Report for application No. 2007201377 dated Mar. 19, 2009, 3 pages.
Canadian Examiner's Requisition for application No. 2582643 dated May 19, 2009, 4 pages.
Canadian Examiner's Requisition for application No. 2582643 dated Mar. 10, 2010, 4 pages.
European Examination Report for application No. 07251388.0 dated Apr. 10, 1008, 4 pages.
Australian Examiner's Report for application No. 2008221593 dated Mar. 30, 3011, 3 pages.
Canadian Examiner's Requisition for application No. 2639776 dated Dec. 21, 2010, 6 pages.
Australian Examiner's Report for application No. 2009200097 dated Jul. 2, 2010, 2 pages.
Australian Examiner's Report for application No. 2011201199 dated May 10, 2011, 2 pages.
European Search Report, Application No. EP 10178982 mailed Nov. 22, 2010.
Japanese Office Action, Application No. JP 2009-006871 mailed Mar. 1, 2011.
European Search Report for European application No. EP 08253148 mailed Nov. 24, 2010, 6 pages.
European Search Report for European application No. EP 10178905, dated Nov. 25, 2010, 7 pages.
Australian Search Report for Australian application No. 2008221593, dated Mar. 29, 2010, 3 pages.
Australian Examiner's first report on Patent Application No. 2009202200, dated Jul. 22, 2010 (3 pages).
(Abstract Only) Kobayashi Yoshiaki et al., Biosensor, JP 61002050, Jan. 8, 1986., </TD></TR>.
Laszlo Daruhazi et al. "Cyclic Voltammetry for Reversible Redox-Electrode Reactions in Thin-Layer Cells With Closely Separated Working and Auxiliary Electrodes of the Same Size" in J. Electroanal. Chem., 264:77-89 (1989).
Osamu, Niwa, et al., "Electrochemical Behavior of Redox Species at Interdigitated Array Electrodes with Different Geometries: Consideration of Redox Cycling and Collection Efficiency," Analytical Chemistry; Mar. 1990, vol. 62, No. 5, pp. 447-452.
Australian Examiner's first report on Patent Application No. 2007201377, dated Jun. 25, 2008.
European Search Report, Application No. EP 09250133, mailed Sep. 15, 2009.
Chinese Office Action for CN 200810175601.0; dated, Nov. 28, 2013, 3 pages.
Chinese Office Action for CN 200810175601.0; dated Nov. 28, 2013 (6 pages).
Japanese Office Action for JP 2012-261693; dated Feb. 12, 2014 (5 pages).
Australian Patent Examination Report for AU 2013202708; dated Feb. 18, 2014 (6 pages).
Australian Patent Examination Report for AU 2013202716; dated Feb. 28, 2014 (3 pages).
Australian Patent Examination Report for AU 2013202702; dated Mar. 11, 2014 (6 pages).
Japanese Office Action for JP 2013-129601; dated Mar. 11, 2014 (2 pages).
Canadian Office Action for CA 2,668,237; dated Jun. 4, 2014 (3 pages).
Indian Examination Report for IN 1627/KOL/2008; dated Mar. 27, 2013 (2 pages).
Japanese Office Action for JP 2014-098994; Dated: Jan. 13, 2015; 2 pages.
Japanese Office Action for JP 2012-261693; Dated: Sep. 2, 2014; 2 pages.
Chinese Office Action and Search Report for CN 201310139029.3; Dated Sep. 3, 2014; 10 pages.
Canadian Office Action for CA 2,748,433; Dated Nov. 3, 2014; 5 pages.
European Office Action for EP 09 250 133.7; Dated: Nov. 17, 2014; 2 pages.
Japanese Office Action for JP 2012-261693; Dated: Mar. 24, 2015; 2 pages.
Australian Patent Examination Report for AU 2013263743; dated: Mar. 25, 2015; 4 pages.
Canadian Office Action ad Examination Search Report for CA 2,648,625; dated: Apr. 7, 2015; 5 pages.

\* cited by examiner

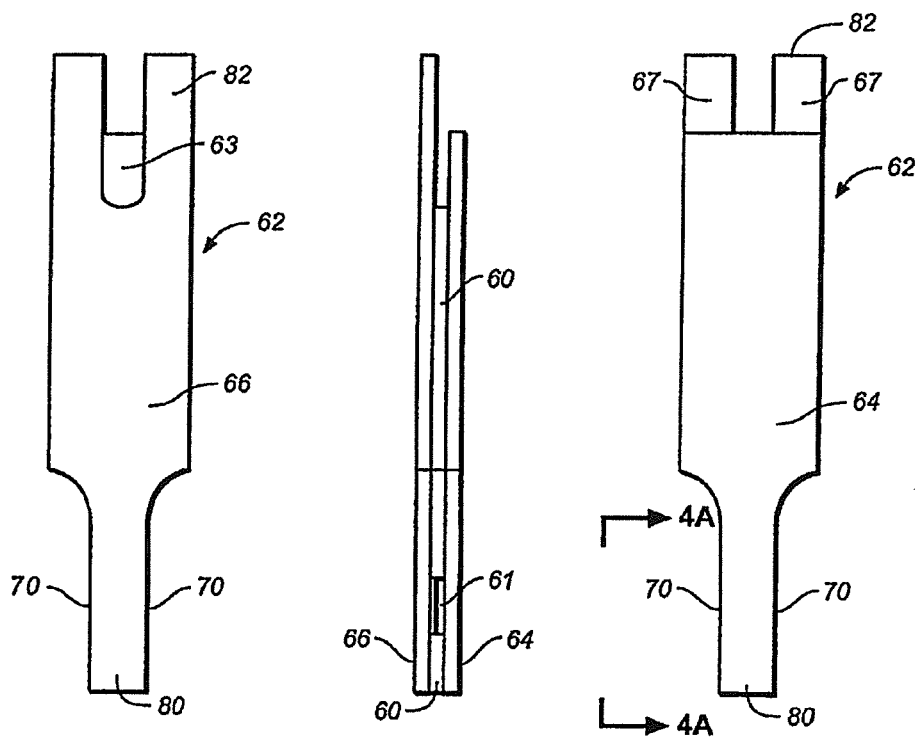
FIG. 2 FIG. 3 FIG. 4A
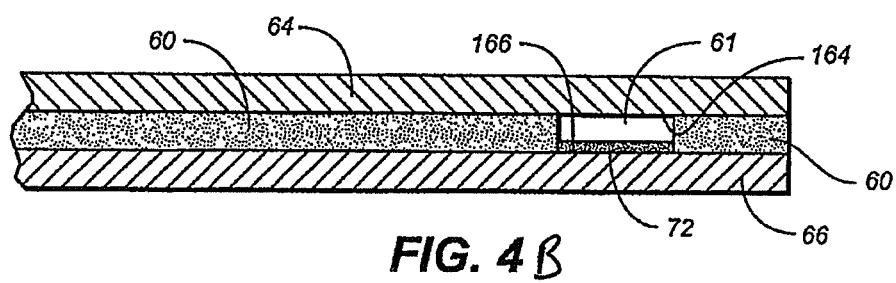
FIG. 4B

SYSTEMS AND METHODS OF DISCRIMINATING CONTROL SOLUTION FROM A PHYSIOLOGICAL SAMPLE

CROSS REFERENCES TO RELATED APPLICATIONS

This application is a divisional application of U.S. patent application Ser. No. 12/211,484, filed Sep. 16, 2008, entitled "Systems and Methods of Discriminating Control Solution From a Physiological Sample", which claims priority under 35 U.S.C. §119 to U.S. Provisional Patent Application Ser. No. 60/976,083, filed Sep. 28, 2007, entitled "Systems and Methods of Discriminating Control Solution From a Physiological Sample", in which the entirety of each of these applications is herein incorporated by reference.

FIELD

The system and method provided herein relates to the field of medical testing, in particular the detection of the presence and/or concentration of an analyte(s) within a sample (e.g., blood).

BACKGROUND

Analyte concentration determination in physiological fluids (e.g., blood or blood derived products such as plasma) is of ever increasing importance to today's society. Such assays find use in a variety of applications and settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like.

A common method for analyte concentration determination assays is based on electrochemistry. In such methods, an aqueous liquid sample is placed into a sample reaction chamber in an electrochemical cell made up of at least two electrodes, i.e., a reference and working electrode, where the electrodes have an impedance that renders them suitable for amperometric or coulometric measurement. The component to be analyzed is allowed to react with a reagent to form an oxidizable (or reducible) substance in an amount proportional to the analyte concentration. The quantity of the oxidizable (or reducible) substance present is then estimated electrochemically and related to the analyte concentration in the sample.

An automated device, e.g., an electrochemical test meter is typically employed for determining the concentration of the analyte in the sample. Many test meters advantageously allow for an analyte concentration, and usually a plurality of analyte concentrations, to be stored in the memory of the meter. This feature provides the user with the ability to review analyte concentration levels over a period of time, often times as an average of previously collected analyte levels, where such averaging is performed according to an algorithm associated with the meter. However, to ensure that the system is functioning properly, the user will occasionally perform a test using a control fluid instead of a blood sample. Such control fluids (also referred to as control solutions) are generally aqueous solutions having a known concentration of glucose. The user can perform a test with the control solution and compare the displayed results with the known concentration to determine if the system is functioning properly. However, once the control solution test is performed, the glucose concentration of the control fluid is stored in the memory of the meter. Thus, when a user seeks to review previous tests and/or the average concentration of previous test results, the results may be skewed to the concentration of the control fluid analyte level.

Thus, it is desirable to be able to distinguish control solutions and sample fluids during a test. One option is to manually flag the fluids as either control or test fluids. However automatic flagging would be preferable since it minimizes user interaction and increases ease-of-use.

As such, there is continued interest in the development of new methods and devices for use in the determination of analyte concentrations in a sample. Of particular interest would be the development of such methods and devices that include the ability to automatically flag a sample as control fluid or test fluid and to store or exclude measurements accordingly. Of particular interest would be the development of such methods that are suitable for use with electrochemical based analyte concentration determination assays.

SUMMARY

Various aspects of a system and method for distinguishing between an aqueous non-blood sample (e.g., a control solution) and a blood sample are provided herein. In one such aspect, the methods include using a test strip in which a potential is applied and a current is measured. Current values are used to determine if a sample is a blood sample or a non-blood sample based on at least one characteristic. Further described herein are methods for calculating a discrimination criterion based upon at least two characteristics. Still further described herein are systems for distinguishing between blood samples and non-blood samples.

In one embodiment, a, method for distinguishing between a blood sample and a non-blood sample is disclosed. The method includes introducing a sample into an electrochemical cell having first and second electrodes and applying a first test potential between the first electrode and the second electrode. A resulting first current transient is then measured. A second test potential is applied between the first electrode and the second electrode and a second current transient is then measured. The method can also include applying a third test potential between the first electrode and the second electrode, and measuring a third current transient.

Based on the first current transient, a first reference value related to the quantity of redox species in the sample is calculated. In addition, based on the second and third current transients, a second reference value related to reaction kinetics is calculated. The first and second reference values are then used to determine whether the sample is a non-blood sample or a blood sample. The non-blood sample can be a control solution or some other sample such as a beverage (e.g., a sports drink such as Gatorade®).

In one aspect, the first reference value is proportional to a concentration of an interferent in the sample. For example, the first reference value can be an interferent index calculated based upon at least one current value from the first current transient. The second reference values can be a function of a percent completion of a chemical reaction. For example, the second reference value can be a residual reaction index calculated based upon at least one current value from the second current transient and at least one current value from the third current transient. In one aspect, the residual reaction index is calculated based upon a ratio of a second current value and a third current value.

In another aspect, the method can perform the step of measuring a concentration of an analyte in the sample. If the sample is found to be a blood sample, the measured concentration can be stored. Conversely, if the sample is found to be a non-blood sample, the measured concentration can be flagged, stored separately, and/or discarded.

In one embodiment, statistical classification can be used to determine if the sample is a non-blood sample or a blood sample. For example, an equation representing an empirically derived discrimination line can be used to evaluate the first and second reference values.

In another aspect, an open-circuit potential is applied to the electrochemical cell before the step of applying the first test potential. In addition, an open-circuit potential can be applied after the step of applying the first test potential.

Further described herein is a system for distinguishing between a blood sample and a non-blood sample. In one embodiment, the system can include a test strip and a test meter. The test strip includes electrical contacts for mating with the test meter and an electrochemical cell. The test meter includes a processor adapted to receive current data from the test strip, and data storage containing discrimination criteria for distinguishing a blood sample from a non-blood sample based on antioxidant concentration and reaction kinetics. The discrimination criteria can be derived from an interferent index that is representative of antioxidant concentration and a residual reaction index that is representative of reaction kinetics. For example, the discrimination criteria can include an empirically derived discrimination line. The system can further include a non-blood sample (e.g., a control solution) that is substantially devoid of redox species.

Still further described herein is a method for calculating a discrimination criterion. The discrimination criterion can be programmed into a test meter for distinguishing between a blood sample and a non-blood sample. In one embodiment, the method includes calculating an interferent index and a residual reaction index for a plurality of control solution samples and calculating a discrimination criterion based on a regression of the interferent index and the residual reaction index for the plurality of non-blood samples.

In one aspect, the discrimination criterion is a discrimination line. For example, the method can include plotting an interferent index and a residual reaction index for a plurality of blood samples and shifting the discrimination line towards the plurality of blood samples.

In one aspect, a method is provided for distinguishing between a blood sample and a control solution which includes (a) applying a first test potential between a first electrode and a second electrode when a sample is introduced into an electrochemical cell and measuring a first current transient, (b) applying a second test potential between a first electrode and a second electrode wherein the second test potential can be sufficient to oxidize a reduced mediator at the second electrode and measuring a second current transient, (c) applying a third test potential between a first electrode and a second electrode wherein the third test potential can be sufficient to oxidize a reduced mediator at the first electrode. Further, the method can include measuring a third current transient. The method can also include (d) calculating, based on the first current transient, a first reference value, (e) calculating, based on the second and third current transients, a second reference value, and (f) determining, based on the first and second reference values, whether the sample is a control solution or blood sample.

The various reference values mentioned above can be determined and/or calculated in various manners. For example, the first reference value can be proportional to a concentration of an interferent in the sample, the first reference value can be calculated based upon at least one current value from the first current transient, or the first reference value can be calculated based upon a summation of current values measured during the first current transient. In an embodiment wherein the first reference value can be calculated based upon a summation of current values measured during the first current transient, the summation can be represented by an equation, the equation being $$i_{sum} = \sum_{t=0.05}^{1} i(t),$$

where $i_{sum}$ is the summation of current values and t is a time.

In other embodiments, the second and third reference values can also be calculated ro determined in various manners. For example, the second reference value can be based on a percent completion of a chemical reaction, the second reference value can be based upon at least one current value from the second current transient and at least one current value from the third current transient, or the second reference value can be based upon a second current value at about the end of the second current transient and a third current value at about the beginning of the third current transient. In other embodiments, the second reference value can be based upon a ratio of the second current value and the third current value wherein the ratio can be represented by an equation, the equation being $$\text{ratio} = \frac{i_2}{i_3},$$

where $i_2$ is the second current value and $i_3$ is the second current value.

In various embodiments of the method, various orientations and/or configurations of various components of a system can be utilized. For example, in one embodiment, the first electrode and the second electrode have an opposing face arrangement wherein a reagent layer can be disposed on the first electrode and not disposed on the second electrode. In another embodiment, the first electrode and the second electrode can have a co-planar arrangement with a reagent layer disposed on the first electrode and not disposed on the second electrode.

Various embodiments of the method can also include various additional or optional steps. For example, in one embodiment, the method can include the step of measuring a concentration of an analyte wherein, for example, if the sample is found to be a control solution the analyte concentration associated with the control sample is flagged. Additionally, in one embodiment, above-identified step (f) can further include using a statistical classification to determine if the sample is a control solution or a blood sample. In another embodiment, above-identified step (f) can further include comparing the first reference value to a pre-determined threshold value, and comparing the second reference value to a pre-determined threshold equation (e.g., a equation which is a function of the first reference value) to determine if the sample is a control solution or a blood sample.

In another aspect, a system for distinguishing between a blood sample and a control solution sample is provided. In one embodiment, the system can include (a) a test strip including electrical contacts for mating with a test meter and an electrochemical cell which includes (i) a first electrode and a second electrode in a spaced apart relationship, and (ii) a reagent. Further, the system can include (b) a test meter including a processor configured to receive current data from the test strip, and data storage containing discrimination criteria for distinguishing a blood sample from a control sample (e.g., a sample being substantially devoid of redox species) based on antioxidant concentration and reaction kinetics.

In various embodiments, the above-mentioned discrimination criteria can be derived from various sources. For example, in one embodiment, the discrimination criteria can be derived from an interferent index that is representative of antioxidant concentration and a residual reaction index that is representative of reaction kinetics. In another embodiment, the discrimination criteria can include an empirically derived discrimination line.

In yet another aspect, a method for calculating a discrimination criteria for programming into a test meter for distinguishing between a blood sample and a control solution sample is provided. In one embodiment, the method can include the steps of (a) calculating an interferent index and a residual reaction index for a plurality of control solution samples and (b) calculating a discrimination criteria based on a regression of the interferent index and the residual reaction index for the plurality of control solution samples. Optionally, the method can further include the step of plotting an interferent index and a residual reaction index for a plurality of blood samples and shifting the discrimination line towards the plurality of blood samples. In one embodiment, the discrimination criteria is a discrimination line.

In another aspect, a method for distinguishing between a blood sample and a control solution sample is provided which includes the step of (a) introducing a sample into an electrochemical cell wherein the cell can include (i) two electrodes in a spaced apart relationship and (ii) a reagent. The method can further include the steps of (b) applying a first test potential, having a first polarity, between the electrodes, and measuring cell current, (c) summing at least two current values measured during the first test potential to generate an interferent index, and (d) using the interferent index to distinguish between a blood sample and a control solution sample.

BRIEF DESCRIPTION OF THE DRAWINGS

Various features of the present disclosure are set forth with particularity in the appended claims. A better understanding of such features can be obtained by reference to the following detailed description that sets forth illustrative, non-limiting embodiments and the accompanying drawings of which:

FIG. 2 is a bottom plan view of the test strip of FIG. 1A;

FIG. 3 is a side plan view of the test strip of FIG. 1A;

FIG. 4A is a top plan view of the test strip of FIG. 1A;

FIG. 4B is an expanded partial side view of the proximal portion of the test strip consistent with arrows 4A-4A of FIG. 4A;

DETAILED DESCRIPTION

Figure 1A:
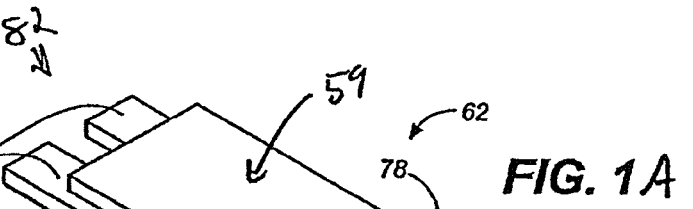
FIG. 1A is a perspective view of an exemplary assembled test strip.
Figure 1B:
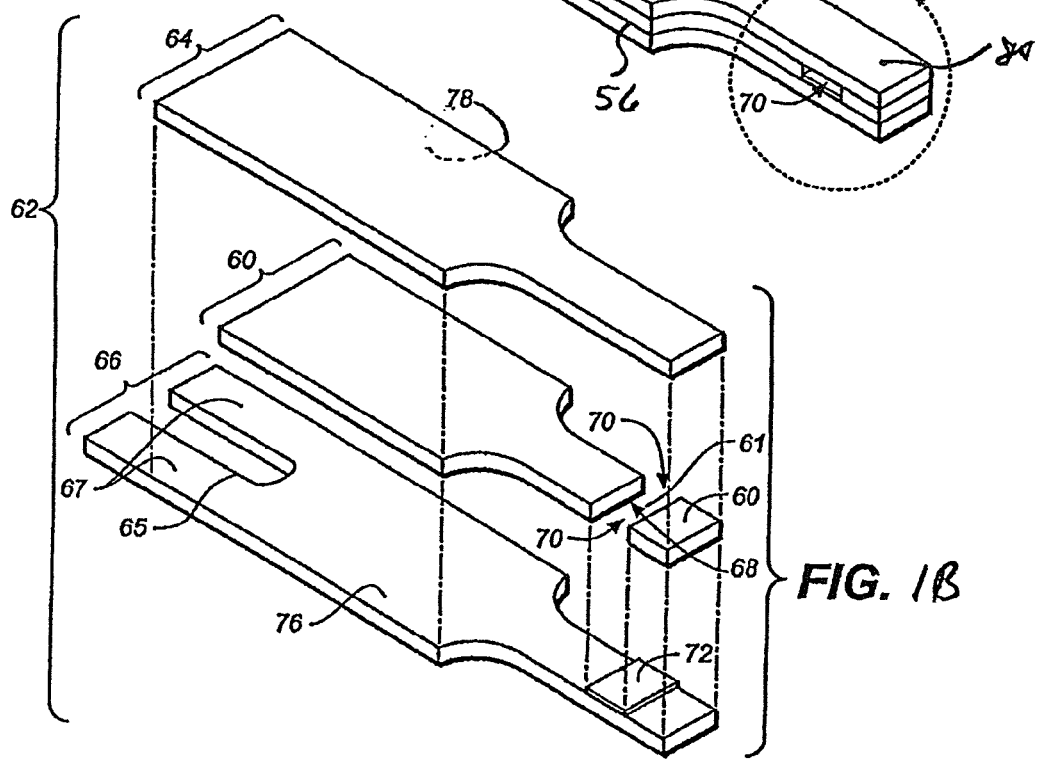
FIG. 1B is an exploded perspective view of the test strip of FIG. 1A.
Figure 1C:
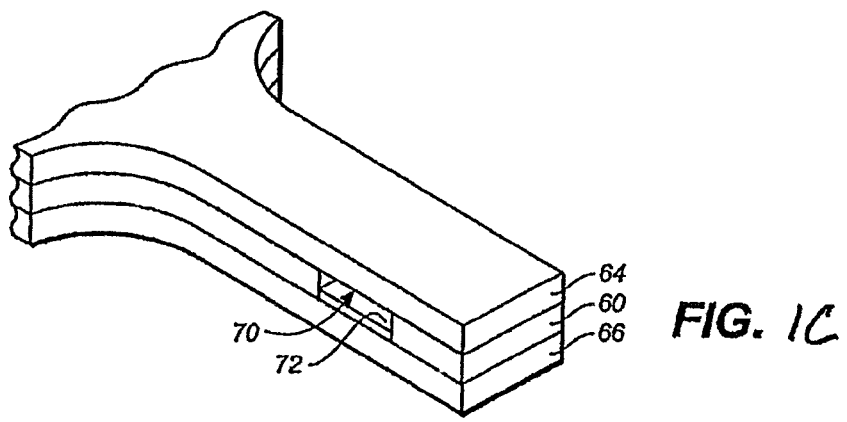
FIG. 1C is an expanded perspective view of a proximal portion of the test strip of FIG. 1A.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The presently disclosed systems and methods are suitable for use in the determination of a wide variety of analytes in a wide variety of samples, and are particularly suited for use in the determination of analytes in whole blood or derivatives thereof, where an analyte of particular interest is glucose. In one aspect, the present disclosure provides various embodiments of a method for determining whether a sample applied to a test strip is an aqueous non-blood sample (e.g., a control solution) or a blood sample. In one such embodiment, at least two characteristics are used to distinguish between a blood sample and non-blood sample. The description will focus on distinguishing between blood samples and control solutions. However, as shown in Example 2 below, the systems and methods provided herein are equally applicable to distinguishing blood samples from any variety of non-blood samples (e.g., beverages, including sports drinks such as Gatorade®).

The methods may be used, in principle, with any type of electrochemical cell having spaced apart first and second electrodes and a reagent layer. For example, an electrochemical cell can be in the form of a test strip. In one aspect, the test strip includes two opposing electrodes separated by a thin spacer layer, where these components define a sample reaction chamber or zone in which is located a reagent layer. One skilled in the art will appreciate that other types of test strips, including, for example, test strips with co-planar electrodes could also be used with the methods described herein.

FIGS. 1A-4B show various views of an exemplary test strip 62 suitable for use with the methods described herein. As shown, the test strip 62 can include an elongate body extending from a proximal end 80 to a distal end 82, and having lateral edges 56, 58. The proximal portion of the body 59 can include a sample reaction chamber 61 having multiple electrodes 164, 166 and a reagent 72, while the distal portion of the test strip body 59 can include features configured for electrically communicating with a test meter. In use, physiological fluid or a control solution can be delivered to the sample reaction chamber 61 for electrochemical analysis.

In the illustrative embodiment, the test strip 62 can include a first electrode layer 66 and a second electrode layer 64, with a spacer layer 60 positioned therebetween. The first electrode layer 66 can provide a first electrode 166 and a first connection track 76 for electrically connecting the first electrode 166 to a first electrical contact 67. Similarly, the second electrode layer 64 can provide a second electrode 164 and a second connection track 78 for electrically connecting the second electrode 164 with a second electrical contact 63.

In one embodiment, the sample reaction chamber 61 is defined by the first electrode 166, the second electrode 164, and a spacer 60 as shown in FIGS. 1A-4B. Specifically, the first electrode 166 and the second electrode 164 define, respectively, the bottom and top of the sample reaction chamber 61. A cutout area 68 of the spacer 60 can define the side walls of the sample reaction chamber 61. In one aspect, the sample reaction chamber 61 can further include a number of ports 70 that provide a sample inlet and/or a vent. For example, one of the ports can provide a fluid sample ingress and the other port can act as a vent.

The sample reaction chamber 61 can have a small volume. For example, the volume can range from about 0.1 microliters to about 5 microliters, preferably about 0.2 microliters to about 3 microliters, and more preferably about 0.3 microliters to about 1 microliter. As will be appreciated by those skilled in the art, the sample reaction chamber 61 can have various other such volumes. To provide the small sample volume, the cutout 68 can have an area ranging from about 0.01 $cm^2$ to about 0.2 $cm^2$, preferably about 0.02 $cm^2$ to about 0.15 $cm^2$, and more preferably about 0.03 $cm^2$ to about 0.08 $cm^2$. Similarly, those skilled in the art will appreciate that the volume cutout 68 can be of various other such areas. In addition, the first and second electrodes 166, 164 can be spaced in the range of about 1 micron to about 500 microns, preferably between about 10 microns and about 400 microns, and more preferably between about 40 microns and about 200 microns. In other embodiments, such a range can vary between various other values. The close spacing of the electrodes can also allow redox cycling to occur, where oxidized mediator generated at the first electrode 166 can diffuse to the second electrode 164 to become reduced, and subsequently diffuse back to the first electrode 166 to become oxidized again.

At the distal end of the test strip body 59, a first electrical contact 67 can be used to establish an electrical connection to a test meter. A second electrical contact 63 can be accessed by the test meter through U-shaped notch 65 as illustrated in FIG. 2. One skilled in the art will appreciate that test strip 62 can include a variety of alternative electrical contacts configured for electrically connecting to a test meter. For example, U.S. Pat. No. 6,379,513, the entirety of which is hereby incorporated herein by reference, discloses an electrochemical cell connection means.

In one embodiment, the first electrode layer 66 and/or the second electrode layer 64 can be a conductive material formed from materials such as gold, palladium, carbon, silver, platinum, tin oxide, iridium, indium, and combinations thereof (e.g., indium doped tin oxide). In addition, the electrodes can be formed by disposing a conductive material onto an insulating sheet (not shown) by various processes such as, for example, a sputtering, electroless plating, or a screen printing process. In one exemplary embodiment, the second electrode layer 64 can be a sputtered gold electrode and the first electrode layer 66 can be a sputtered palladium electrode. Suitable materials that can be employed as the spacing layer 60 include various insulating materials, such as, for example, plastics (e.g., PET, PETG, polyimide, polycarbonate, polystyrene), silicon, ceramic, glass, adhesives, and combinations thereof.

A reagent layer 72 can be disposed within sample reaction chamber 61 using a process such as slot coating, dispensing from the end of a tube, ink jetting, and screen printing. Such processes are described, for example, in the following U.S. Pat. Nos. 6,749,887; 6,869,411; 6,676,995; and 6,830,934, the entirety of each of these references being incorporated herein by reference. In one embodiment, the reagent layer 72 can include at least a mediator and an enzyme, and can be deposited onto the first electrode 166. Various mediators and/or enzymes are within the spirit and scope of the present disclosure. For example, suitable mediators include ferricyanide, ferrocene, ferrocene derivatives, osmium bipyridyl complexes, and quinone derivatives. Examples of suitable enzymes include glucose oxidase, glucose dehydrogenase (GDH) based on pyrroloquinoline quinone (PQQ) co-factor, GDH based on nicotinamide adenine dinucleotide co-factor, and FAD-based GDH [E.C.I.1.99.10]. One exemplary reagent formulation, which would be suitable for making the reagent layer 72, is described in pending U.S. application Ser. No. 10/242,951, entitled, Method of Manufacturing a Sterilized and Calibrated Biosensor-Based Medical Device, published as U.S. Published Patent Application No. 2004/0120848, the entirety of which is hereby incorporated herein by reference.

Either the first electrode 166 or the second electrode 164 can function as working electrode which oxidizes or reduces a limiting amount of mediator depending on the polarity of the applied test potential of the test meter. For example, if the current limiting species is a reduced mediator, it can be oxidized at the first electrode 166 as long as a sufficiently positive potential was applied with respect to the second electrode 164. In such a situation, the first electrode 166 performs the function of the working electrode and the second electrode 164 performs the function of a counter/reference electrode. It should be noted that unless otherwise stated for test strip 62, all potentials applied by test meter 100 will hereinafter be stated with respect to second electrode 164.

Similarly, if a sufficiently negative potential is applied with respect to the second electrode 164, then the reduced mediator can be oxidized at the second electrode 164. In such a situation, the second electrode 164 can perform the function of the working electrode and the first electrode 166 can perform the function of the counter/reference electrode.

A first step in an embodiment of the presently disclosed method can include introducing a quantity of the fluid sample of interest into the test strip 62, which includes the first electrode 166, the second electrode 164 and a reagent layer 72. The fluid sample can be whole blood or a derivative or fraction thereof, or a control solution. The fluid sample, e.g., blood, can be dosed into the sample reaction chamber 61 via the port 70. In one aspect, port 70 and/or the sample reaction chamber 61 can be configured such that capillary action causes the fluid sample to fill the sample reaction chamber 61.

Figure 5:
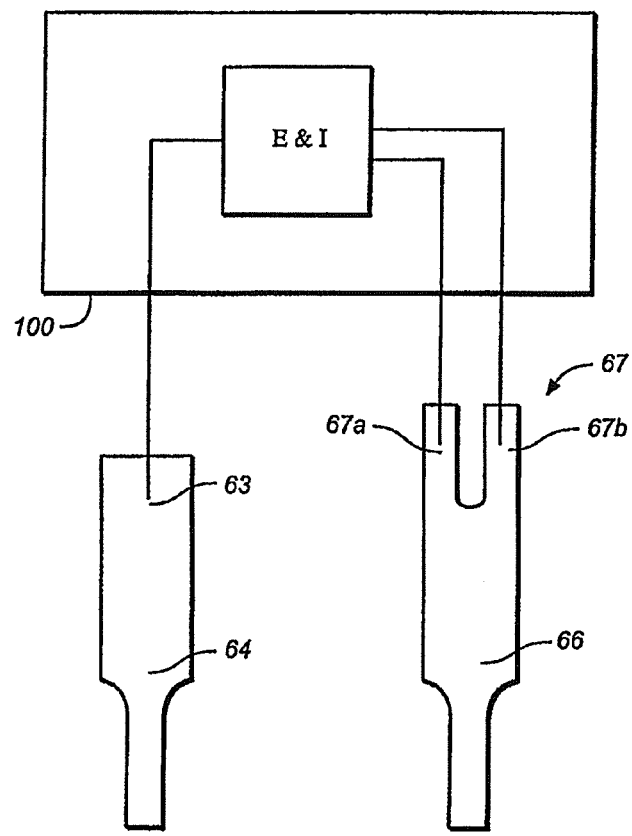
FIG. 5 is a simplified schematic showing a test meter electrically interfacing with portions of the test strip.

FIG. 5 provides a simplified schematic showing a test meter 100 interfacing with a first electrical contact 67 and a second electrical contact 63, which are in electrical communication with the first electrode 166 and the second electrode 164, respectively, of the test strip 62. Test meter 100 can be configured to electrically connect to the first electrode 166 and the second electrode 164, via the first electrical contact 67 and the second electrical contact 63, respectively (as shown in FIGS. 2 and 5). As will be appreciated by those skilled in the art, a variety of test meters can be used with the method described herein. However, in one embodiment, the test meter includes at least a processor configured for performing calculations capable of discriminating between blood and a control sample, as well as configured for data sorting and/or storage.

As illustrated in FIG. 5, an electrical contact 67 can include two prongs 67a and 67b. In one exemplary embodiment, the test meter 100 separately connects to the prongs 67a and 67b, such that when the test meter 100 interfaces with a test strip 62, a circuit is completed. The test meter 100 can measure the resistance or electrical continuity between the prongs 67a and 67b to determine whether the test strip 62 is electrically connected to the test meter 100. One skilled in the art will appreciate that the test meter 100 can use a variety of sensors and circuits to determine when the test strip 62 is properly positioned with respect to the test meter 100.

In one embodiment, the test meter 100 can apply a test potential and/or a current between first electrical contact 67 and second electrical contact 63. Once the test meter 100 recognizes that a test strip 62 has been inserted, the test meter 100 turns on and initiates a fluid detection mode. In one embodiment, the fluid detection mode causes the test meter 100 to apply a constant current of 1 microampere between the first electrode 166 and the second electrode 164. Because the test strip 62 is initially dry, the test meter 100 measures a maximum voltage, which is limited by the hardware within the test meter 100. However, once a user doses a fluid sample onto the inlet 70, this causes the sample reaction chamber 61 to become filled. When the fluid sample bridges the gap between the first electrode 166 and the second electrode 164, the test meter 100 will measure a decrease in measured voltage (e.g., as described in U.S. Pat. No. 6,193,873, the entirety of which being incorporated herein by reference), which is below a predetermined threshold causing the test meter 100 to automatically initiate the glucose test.

It should be noted that the measured voltage may decrease below a pre-determined threshold when only a fraction of the sample reaction chamber 61 has been filled. A method of automatically recognizing that a fluid was applied does not necessarily indicate that the sample reaction chamber 61 has been completely filled, but can only confirm a presence of some amount of fluid in the sample reaction chamber 61. Once the test meter 100 determines that a fluid has been applied to the test strip 62, a short, but no-zero amount of time may still be required to allow the fluid to completely fill the sample reaction chamber 61.

Figure 6:
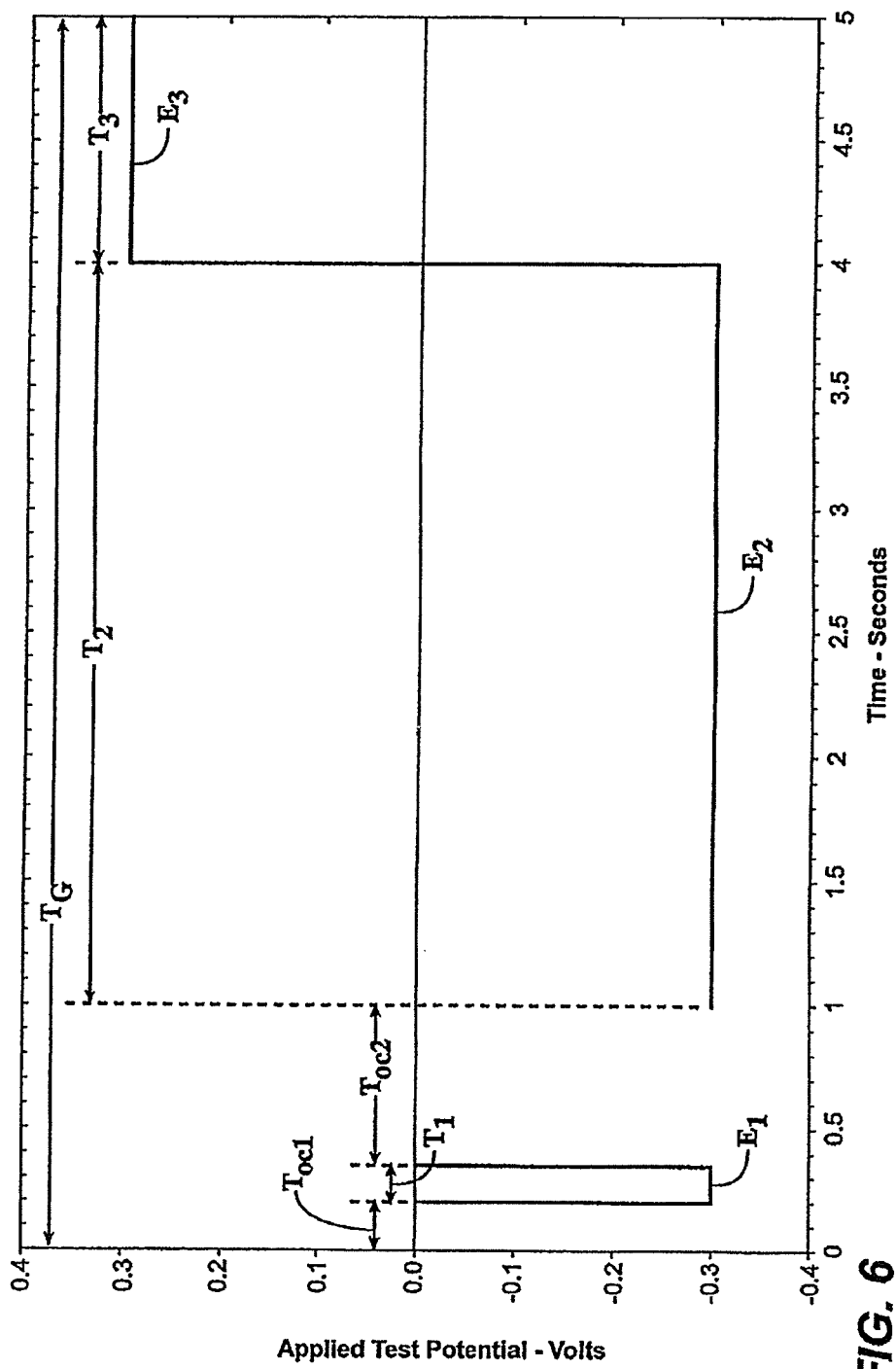
FIG. 6 shows an example of a potential waveform in which the test meter applies a series of open-circuit potentials and test potentials for prescribed time intervals.

In one embodiment, once the test meter 100 has determined that a fluid has been introduced (e.g., dosed) onto the test strip 62, a test meter 100 can perform a glucose test by applying a plurality of open-circuit potentials and a plurality of test potentials to the test strip 62 for prescribed intervals as shown in FIG. 6. A glucose test time interval $T_G$ represents an amount of time to perform the glucose test (but not necessarily all the calculations associated with the glucose test) where glucose test time interval $T_G$ can include a first open-circuit time interval $T_{OC1}$, a first test potential time interval $T_1$, a second open-circuit time interval $T_{OC2}$, a second test potential time interval $T_2$, and a third test potential time interval $T_3$. The glucose test time interval $T_G$ can range, for example, from about 1 second to about 5 seconds. While the two open-circuit time intervals and the three test potential time intervals are described, one skilled in the art will appreciate that the glucose test time interval can include different numbers of open-circuit and test potential time intervals. For example, the glucose test time interval could include a single open-circuit time interval and/or only two test potential time intervals.

Once the glucose assay has been initiated, the test meter 100 switches to a first open-circuit for a first open-circuit potential time interval $T_{OC1}$, which in the illustrated embodiment is about 0.2 seconds. In another embodiment, first open-circuit time interval $T_{OC1}$ can be in the range of about 0.05 seconds to about 2 seconds and preferably between about 0.1 seconds to about 1.0 seconds, and most preferably between about 0.15 seconds to about 0.6 seconds.

One of the reasons for implementing the first open-circuit is to allow sufficient time for the sample reaction chamber 61 to fill or partially fill with sample. Typically, at ambient temperature (i.e., 22° C.), the sample reaction chamber 61 takes about 0.1 seconds to about 0.5 seconds to completely fill with blood. Conversely, at ambient temperature, the sample reaction chamber 61 takes about 0.2 seconds or less to completely fill with control solution, where the control solution is formulated to have a viscosity of about 1 to about 3 centipoise.

While the control solutions are composed of known components and are generally uniform, blood samples can vary in their make-up and/or composition. For example, high hematocrit blood samples are more viscous than low hematocrit blood samples, therefore higher hematocrit blood samples require additional time to fill compared with lower hematocrit blood samples. Thus, depending on a variety of factors, blood sample filling time can vary.

Figure 7:
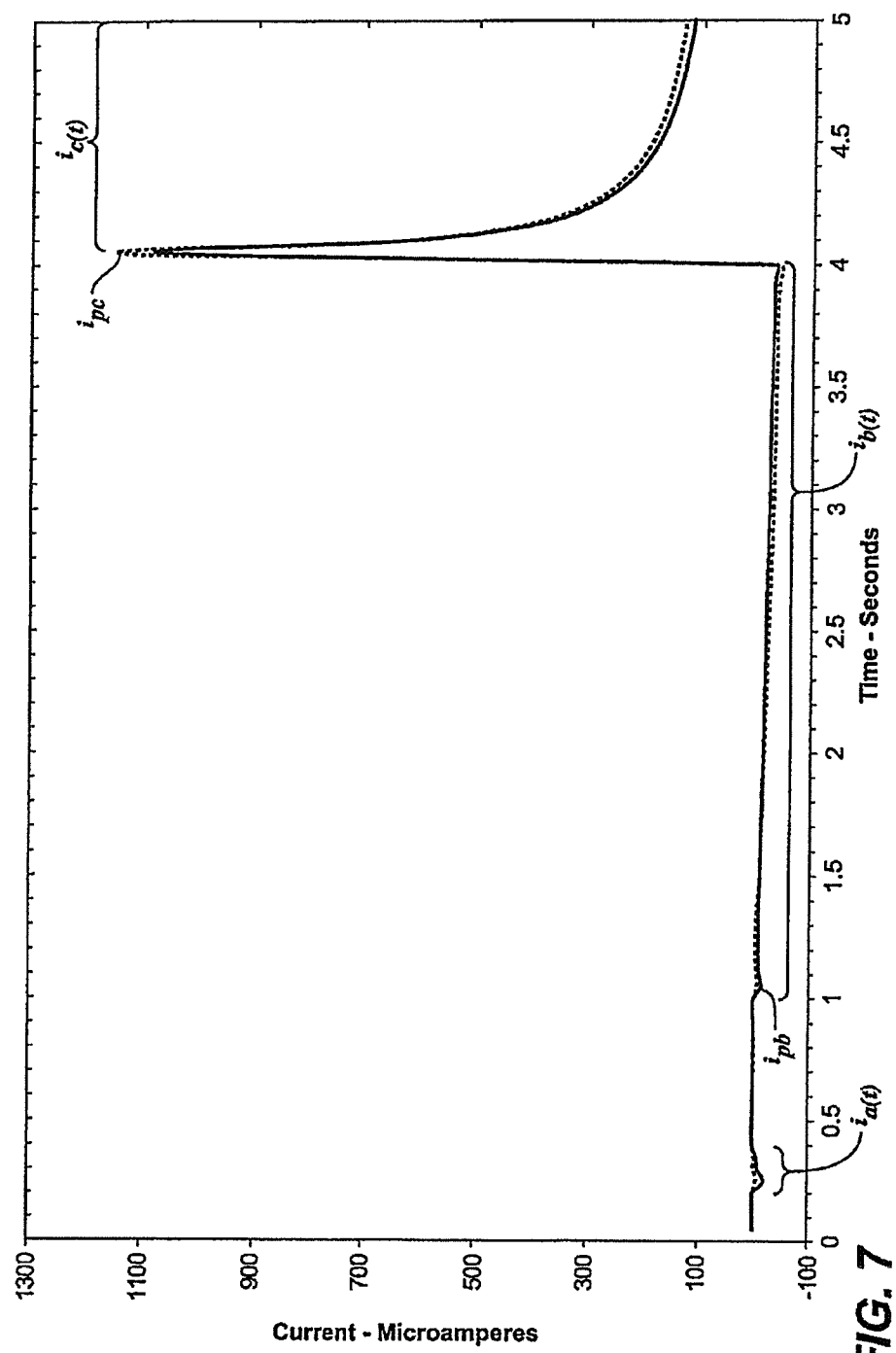
FIG. 7 shows a current transient generated by the test meter that is testing the test strip with the potential waveform of FIG. 6 with a control solution sample (CS, dotted line) and a blood sample (BL, solid line)

After applying the first open-circuit potential, the test meter 100 applies a first test potential $E_1$ between the first electrode 166 and the second electrode 164 (e.g., −0.3 Volts in FIG. 6), for a first test potential time interval $T_1$ (e.g., 0.15 seconds in FIG. 6). The test meter 100 measures the resulting first current transient, which can be referred to as $i_a(t)$ as shown in FIG. 7. A current transient represents a plurality of current values measured by a test meter during a particular test potential time interval. In one embodiment, first test potential time interval $T_1$ can be in the range of about 0.05 seconds to about 1.0 second and preferably between about 0.1 seconds to about 0.5 seconds, and most preferably between about 0.1 seconds to about 0.2 seconds. In other embodiments, the first test potential time interval $T_1$ can include any other desired time ranges.

As discussed below, a portion or all of the first current transient can be used in the methods described herein to determine whether control solution or a blood sample was applied to the test strip 62. The magnitude of the first transient current is effected by the presence of easily oxidizable substances in the sample. Blood usually contains endogenous and exogenous compounds that are easily oxidized at the second electrode 164. Conversely, the control solution can be formulated such that it does not contain oxidizable compounds. However, blood sample composition can vary and the magnitude of the first current transient for high viscosity blood samples will be smaller than low viscosity samples (in some cases even less than the control solution samples) because the sample reaction chamber 61 may not be completely filled after about 0.2 seconds. An incomplete fill will cause the effective area of the first electrode 166 and the second electrode 164 to decrease which in turn causes the first current transient to decrease. Thus, the presence of oxidizable substances in a sample, by itself, is not always a sufficient discriminatory factor because of variations in blood samples.

After the test meter 100 stops applying the first test potential $E_1$, it can be configured to switch to a second open-circuit for a second open-circuit time interval $T_{OC2}$, which in the example of FIG. 6, is about 0.65 seconds. In another embodiment, a second open-circuit time interval $T_{OC2}$ can be in the range of about 0.1 seconds to about 2.0 seconds and preferably between about 0.3 seconds to about 1.5 seconds, and most preferably between about 0.5 seconds to about 1.0 seconds. In other embodiments, the second open-circuit time interval $T_{OC2}$ can be any other time interval as desired.

One of the reasons for implementing the second open-circuit is to provide sufficient time for the sample reaction chamber 61 to completely fill, to allow the reagent layer 72 to dissolve, and to allow reduced mediator and oxidized mediator to re-equilibrate at the respective first electrode 166 and second electrode 164 from the perturbation caused by first test potential $E_1$. Although the sample reaction chamber 61 typically fills rapidly, the second open-circuit time interval $T_{OC2}$ can be sufficiently long to account for conditions which can cause fill times to increase, such as low ambient temperature (e.g., about 5° C.) and high hematocrit (e.g., >60% hematocrit).

During the first test potential $E_1$, a reduced mediator can be depleted at the second electrode 164 and generated at the first electrode 166 to form a concentration gradient. The second open-circuit potential provides time for the reduced mediator concentration profile to become closer to the state immediately before the first test potential $E_1$ was applied. As will be described below, a sufficiently long second open-circuit potential is useful because it can allow for glucose concentration to be calculated in the presence of interferents.

An alternative embodiment test potential $E_1'$ can be applied between the electrodes for a duration between when the meter detects that the strip is filling with sample and before a second test potential $E_2$ is applied. In one aspect, test potential $E_1'$ is small. For example, the potential can be between about −1 to about −100 mV, preferably between about −5 mV and about −50 mV and most preferably between about −10 mV and about −30 mV. The smaller potential perturbs the reduced mediator concentration gradient to a lesser extent compared to applying a larger potential difference, but is still sufficient to obtain a measure of the oxidizable substances in the sample. The test potential $E_1'$ can be applied for a portion of the time between detection of fill and when the second test potential $E_2$ is applied or can be applied for the whole of that time period. If the test potential $E_1'$ is to be used for a portion of the time, then an open-circuit could be applied for the remaining portion of the time. The combination of number of open-circuit and small voltage potential applications, their order and times applied is not critical in this embodiment, as long as the total period for which the small potential $E_1'$ is applied is sufficient to obtain a current measurement indicative of the presence and/or quantity of oxidizable substances present in the sample. In a preferred embodiment, the small potential $E_1'$ is applied for substantially the entire period between when a fill is detected and when the second test potential $E_2$ is applied.

Once the second open-circuit time interval $T_{OC2}$ or an equivalent time in the small potential $E_1'$ embodiment has elapsed, the test meter 100 can apply a second test potential $E_2$ between the first electrode 166 and the second electrode 164 for a second test potential time interval $T_2$. During the second test potential time interval $T_2$, the test meter 100 can measure a second current transient $i_b(t)$. After the second potential time interval $T_2$ has elapsed, the test meter 100 can apply a third test potential $E_3$ between the first electrode 166 and the second electrode 164 for a third test potential time interval $T_3$, which may be referred to as $i_c(t)$. The second potential time interval $T_2$ and the third test potential time interval $T_3$ can each range from about 0.1 seconds to about 4 seconds. For the embodiment shown in FIG. 6, the second test potential time interval $T_2$ was about 3 seconds and the third test potential time interval $T_3$ was about 1 second. As mentioned above, an open circuit potential time period can be allowed to elapse between the second test potential $E_2$ and the third test potential $E_3$. Alternatively, the third test potential $E_3$ can be applied following the application of the second test potential $E_2$. Note that a portion of the first, second, or third current transient may be generally referred to as a cell current or a current value.

In one embodiment, the first test potential $E_1$ and the second test potential $E_2$ both have a first polarity, and the third test potential $E_3$ has a second polarity, which is opposite to the first polarity. However, one skilled in the art will appreciate the polarity of the first, second, and third test potentials can be chosen depending on the manner in which analyte concentration is determined and/or depending on the manner in which test samples and control solutions are distinguished.

The first test potential $E_1$ and the second test potential $E_2$ can be sufficiently negative in magnitude with respect to the second electrode 164 such that the second electrode 164 functions as a working electrode in which a limiting oxidation current is measured. Conversely, the third test potential $E_3$ can be sufficiently positive in magnitude with respect to the second electrode 164 such that first electrode 166 functions as a working electrode in which a limiting oxidation current is measured. A limiting oxidation occurs when all the oxidizable species have been locally depleted at the working electrode surface such that the measured oxidation current is proportional to the flux of oxidizable species diffusing from the bulk solution towards the working electrode surface. The term "bulk solution" refers to a portion of the solution sufficiently far away from the working electrode where the oxidizable species was not located within the depletion zone. The first test potential $E_1$, the second test potential $E_2$, and the third test potential $E_3$ can range from about −0.6 Volts to about +0.6 Volts (with respect to the second electrode 164) when using either a sputtered gold or palladium working electrode and a ferricyanide mediator.

Figure 8:
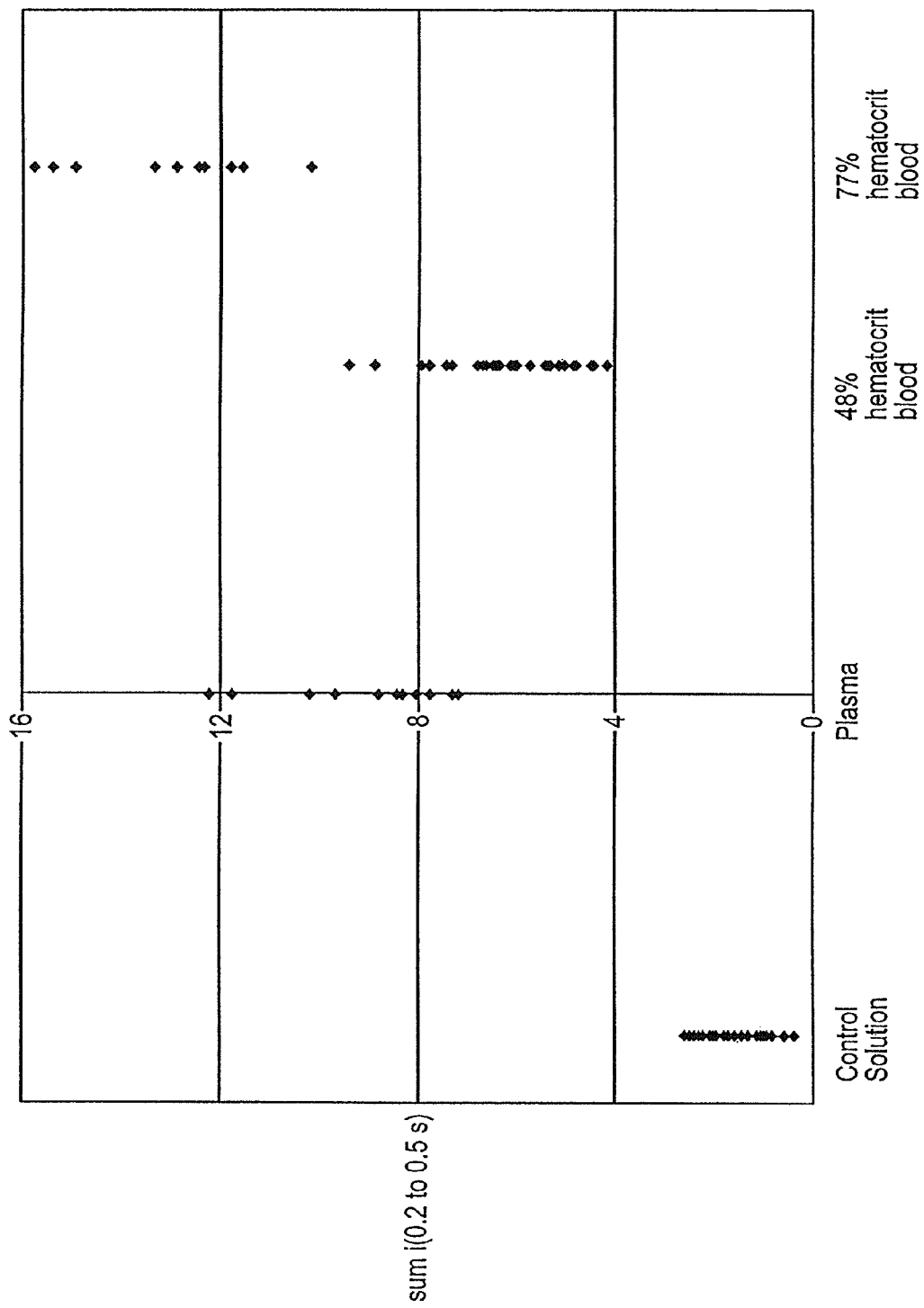
FIG. 8 shows the summation of current values at 0.2 and 0.5 seconds for a control solution, plasma, a blood sample with 48% hematocrit, and a blood sample with 77% hematocrit when a potential of 20 mV was applied.

FIG. 7 shows first, second, and third current transients generated by a test meter 100 and a test strip 62 using either a control solution sample (dotted line) or a blood sample (solid line). The control solution sample contained a 525 mg/dL glucose concentration and the blood sample contained a 530 mg/dL glucose concentration with about 25% hematocrit. FIG. 8 shows an expanded view of first and second current transients in FIG. 7. FIGS. 7 and 8 show the resulting current transients when applying the potential waveform shown in FIG. 6. The description below details how the current transients can be converted into an accurate glucose measurement for the test solution or control solution.

Figure 12:
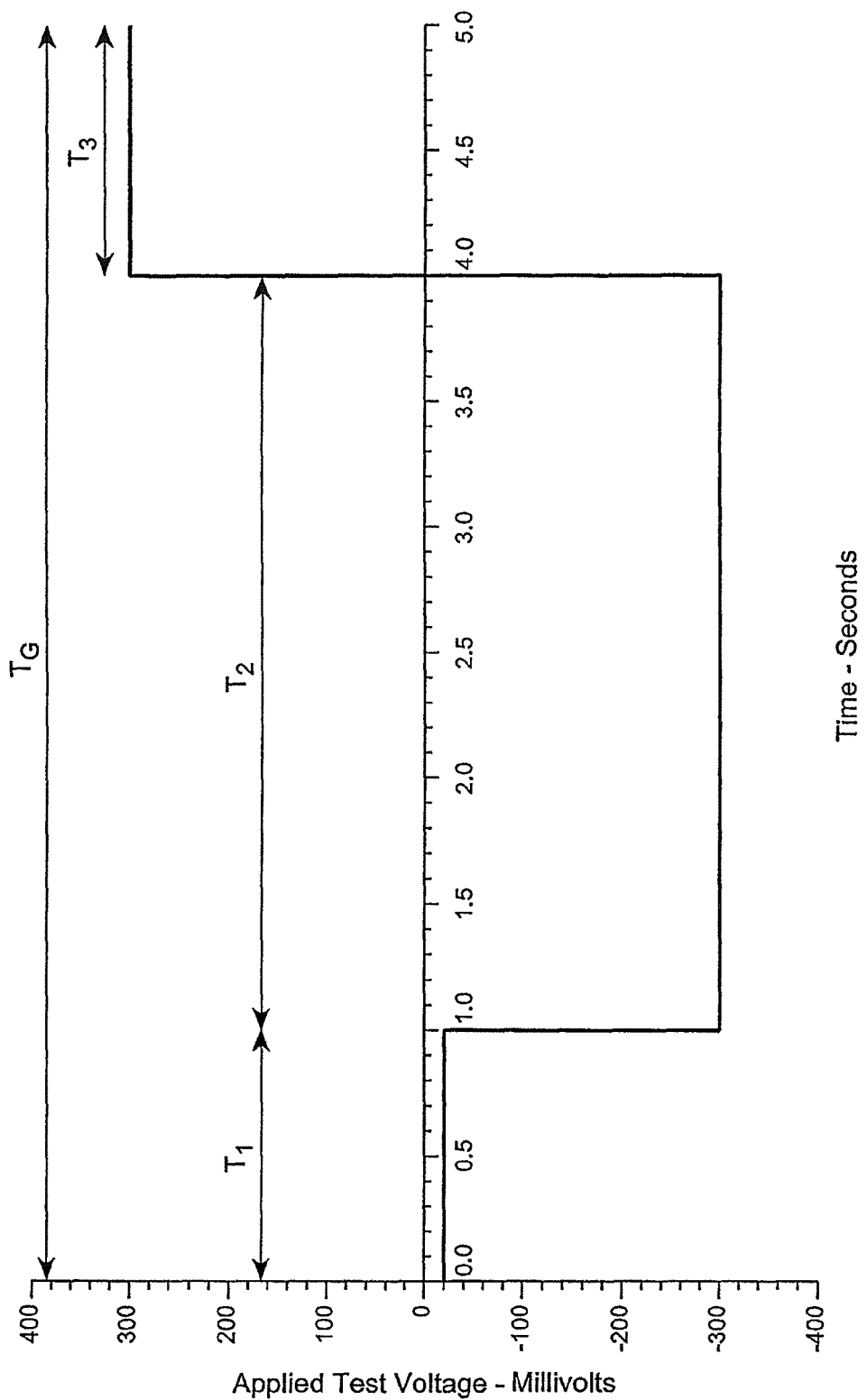
FIG. 12 shows an example of another embodiment of a test potential waveform in which the test meter applies a plurality of test voltages for prescribed time intervals.

As illustrated in FIG. 12, the test meter 100 can perform a glucose test by applying a plurality of test potentials for prescribed intervals. The plurality of test potentials may include a first test potential $E_1'$ for a first test potential time interval $T_1$, a second test potential $E_2$ for a second test potential time interval $T_2$, and a third test potential $E_3$ for a third test potential time interval $T_3$. The plurality of test current values measured during the first, second, and third test potential time intervals may be performed at a frequency ranging from about 1 measurement per nanosecond to about one measurement per 100 milliseconds. One skilled in the art will appreciate that names "first," "second," and "third" are chosen for convenience and do not necessarily reflect the order in which the test potentials are applied.

Figure 13:
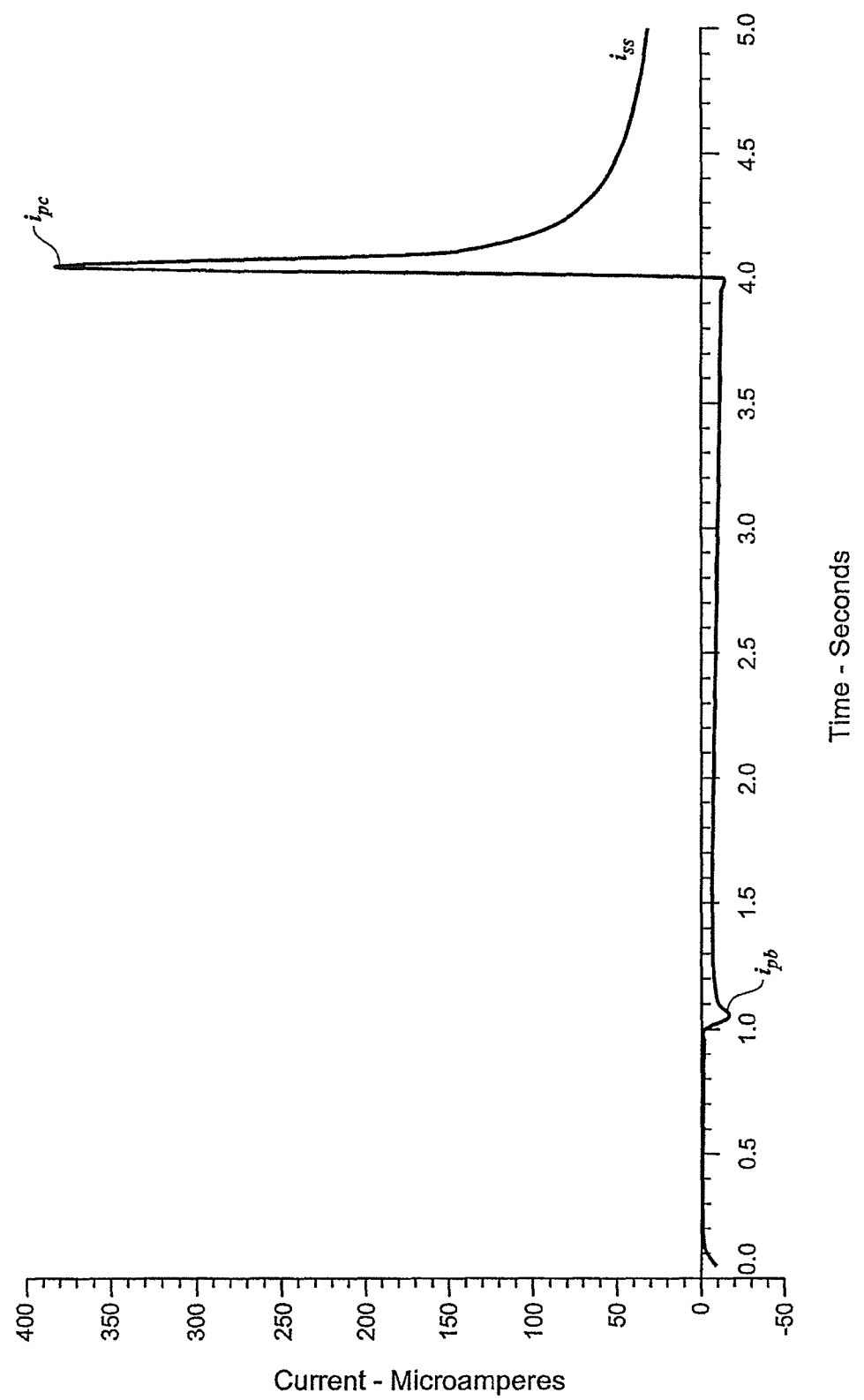
FIG. 13 shows a test current transient generated with the test voltage waveform of FIG. 12.

Once the glucose assay has been initiated using the test potential waveform of FIG. 12, test meter 100 may apply a first test potential $E_1'$ (e.g., −20 mV) for a first test potential time interval $T_1$ (e.g., between 0 and 1 second). The first test potential time interval $T_1$ can range from about 0.1 seconds to about 3 seconds and preferably range from about 0.2 seconds to about 2 seconds, and most preferably range from about 0.3 seconds to about 1 second. The first test potential time interval $T_1$ may be sufficiently long so that the sample reaction chamber 61 can fully fill with sample and also so that the reagent layer 72 can at least partially dissolve or solvate. In one aspect, the first test potential $E_1'$ may be a value relatively close to the redox potential of the mediator so that a relatively small amount of a reduction or oxidation current is measured. FIG. 13 shows that a relatively small amount of current may be observed during the first test potential time interval compared to during the second and third test potential time intervals. For example, when using ferricyanide and/or ferrocyanide as the mediator, the first test potential $E_1'$ can range from about −100 mV to about −1 mV, preferably range from about −50 mV to about −5 mV, and most preferably range from about −30 mV to about −10 mV.

After applying the first test potential $E_1'$, the test meter 100 can apply a second test potential $E_2$ between the first electrode 166 and the second electrode 164 (e.g., about −0.3 Volts, as illustrated in FIG. 12), for a second test potential time interval $T_2$ (e.g., 3 seconds, as illustrated in FIG. 12). The second test potential $E_2$ may be a value sufficiently negative of the mediator redox potential so that a limiting oxidation current occurs at the second electrode 164. For example, when using ferricyanide and/or ferrocyanide as the mediator, the second test potential $E_2$ can range from about −600 mV to about zero mV, preferably range from about −600 mV to about −100 mV, and more preferably be about −300 mV.

The second test potential time interval $T_2$ may be sufficiently long to monitor the rate of generation of reduced mediator (e.g., ferrocyanide) in the sample reaction chamber 61 based on the magnitude of a limiting oxidation current. The reduced mediator may be generated by a series of chemical reactions in the reagent layer 72. During the second test potential time interval $T_2$, a limiting amount of reduced mediator is oxidized at the second electrode 164 and a non-limiting amount of oxidized mediator is reduced at the first electrode 166 to form a concentration gradient between the first electrode 166 and the second electrode 164. As will be described, the second test potential time interval $T_2$ should be sufficiently long so that a sufficient amount of ferricyanide can be generated at the second electrode 164. A sufficient amount of ferricyanide may be required at the second electrode 164 so that a limiting current can be measured for oxidizing ferrocyanide at the first electrode 166 during the third test potential $B_3$. The second test potential time interval $T_2$ can range from about 0 seconds to about 60 seconds and preferably range from about 1 second to about 10 seconds, and most preferably range from about 2 seconds to about 5 seconds.

FIG. 13 shows a relatively small peak at the beginning of the second test potential time interval $T_2$ followed by a gradual increase of an absolute value of an oxidation current during the second test potential time interval (e.g., between about 1 second to about 4 seconds). The small peak occurs due to an initial depletion of reduced mediator at about 1 second. The gradual increase in oxidation current is ascribed to the generation of ferrocyanide by reagent layer 72 followed by its diffusion to the second electrode 164.

After applying the second test potential $E_2$, the test meter 100 can apply a third test potential $B_3$ between the first electrode 166 and the second electrode 164 (e.g., +0.3 Volts in FIG. 12), for a third test potential time interval $T_3$ (e.g., between about 4 to about 5 seconds as illustrated in FIG. 12). The third test potential $B_3$ may be a value sufficiently positive of the mediator redox potential so that a limiting oxidation current is measured at the first electrode 166. For example, when using ferricyanide and/or ferrocyanide as the mediator, the third test potential $E_3$ can range from about zero mV to about 600 mV, preferably range from about 100 mV to about 600 mV, and more preferably be about 300 mV.

The third test potential time interval $T_3$ may be sufficiently long to monitor the diffusion of reduced mediator (e.g., ferrocyanide) near the first electrode 166 based on the magnitude of the oxidation current. During the third test potential time interval $T_3$, a limiting amount of reduced mediator is oxidized at the first electrode 166 and a non-limiting amount of oxidized mediator is reduced at the second electrode 164. The third test potential time interval $T_3$ can range from about 0.1 seconds to about 5 seconds and preferably range from about 0.3 seconds to about 3 seconds, and most preferably range from about 0.5 seconds to about 2 seconds.

FIG. 13 shows a relatively large peak at the beginning of the third test potential time interval $T_3$ followed by a decrease to a steady-state current. In one embodiment, the second test potential $B_2$ may have a first polarity and third test potential $E_3$ may have a second polarity that is opposite to the first polarity. However, one skilled in the art will appreciate the polarity of the second and third test potentials can be chosen depending on the manner in which analyte concentration is determined.

Assuming that a test strip has an opposing face or facing arrangement as shown in FIGS. 1A-4B, and that a potential waveform is applied to the test strip as shown in FIG. 6, a glucose concentration can be calculated using a glucose algorithm as shown in Equation (Eq.) 1:

$$[G] = \left(\frac{i_2}{i_3}\right)^p \times (a \times i_1 - Z) \qquad \text{Eq. 1}$$

In Eq. 1, [G] is the glucose concentration, $i_1$ is a first current value, $i_2$ is a second current value, and $i_3$ is a third current value, and the terms p, Z, and a are empirically derived calibration constants. A derivation of Eq. 1 can be found in a pending U.S. Published Patent Application No. 2007/0074977 (U.S. application Ser. No. 11/240,797), filed on Sep. 30, 2005, and entitled "Method and Apparatus for Rapid Electrochemical Analysis", the entirety of which is hereby incorporated herein by reference. The first current value $i_1$ and the second current value $i_2$ are calculated from the third current transient and $i_3$ is calculated from the second current transient. One skilled in the art will appreciate that names "first," "second," and "third" are chosen for convenience and do not necessarily reflect the order in which the current values are calculated. In addition, all current values (e.g., $i_1$, $i_2$, and $i_3$) stated in Eq. 1 use the absolute value of the current.

In another embodiment, the term $i_1$ can be defined to include peak current values from the second and third current transients to allow for more accurate glucose concentrations in the presence of interferents as shown in Eq. 2:

$$i_1 = i_2 \left\{ \frac{i_{pc} - 2i_{pb} + i_{ss}}{i_{pc} + i_{ss}} \right\} \qquad \text{Eq. 2}$$

The term $i_{pb}$ represents a peak current value for the second test potential time interval $T_2$ and the term $i_{pc}$ represents a peak current value for the third test potential time interval $T_3$. The term $i_{ss}$ is the steady-state current, which is the current predicted to occur at long times after the application of the third test potential $E_3$ in the absence of on-going chemical reactions. Where Eq. 2 is used, the second open-circuit potential time interval $T_{OC2}$ is preferably sufficiently long so as to allow Eq. 2 to compensate for the presence of interferents. When the second open-circuit potential time interval $T_{OC2}$ is too short, the second peak current value $i_{pb}$ can become distorted and can reduce the effectiveness of the interferent correction calculations. The use of peak current values to account for interferents in a physiological sample are described in U.S. Published Patent Application No. 2007/0227912 (U.S. patent application Ser. No. 11/278/341), filed on Mar. 31, 2006 and entitled "Methods and Apparatus for Analyzing a Sample in the Presence of Interferents", the entirety of which is incorporated by reference in its entirety.

In one embodiment, Eq. 1 and Eq. 2 can be used together to calculate a glucose concentration for either blood or a control solution. In another embodiment, the algorithm of Eq. 1 and Eq. 2 can be used for blood with a first set of calibration factors (i.e. a, p, and Z) and a second set of calibration factors can be used for the control solution. When using two different sets of calibration factors, the methods described herein for discriminating between a test fluid and a control solution can improve the effectiveness of the analyte concentration calculations.

In addition, if the test meter determines that the sample type is control solution (as opposed to blood), the test meter can store the resulting glucose concentration of the control sample such that a user can review test sample concentration data separately from control solution data. For example, the glucose concentrations for control solutions can be stored in a separate database, can be flagged, and/or discarded (i.e., not stored or stored for a short period of time).

Another advantage of being able to recognize a control solution is that a test meter can be programmed to automatically compare the results (e.g., glucose concentration) of the test of the control solution with the expected glucose concentration of the control solution. For example, the test meter can be pre-programmed with the expected glucose level(s) for the control solution(s). Alternatively, a user could input the expected glucose concentration for the control solution. When the test meter recognizes a control solution, the test meter can compare the measured control solution glucose concentration with the expected glucose concentration to determine if the meter is functioning properly. If the measured glucose concentration is out of the expected range, the test meter can output a warning message to alert the user.

In one embodiment, the method described herein uses the presence of redox species to distinguish a control solution from a blood sample. The method can include the step of applying a first test potential $E_1'$ and using one or more current values measured during the test potential as a discriminator. In one aspect, two current values from the first test potential $E_1'$ are summed and used as the discriminator. FIG. 8 shows data for a control solution, plasma, a blood sample with 48% hematocrit, and a blood sample is 77% hematocrit. A potential of about 20 mV was applied for the first 1 second and current values at about 0.2 to about 0.5 seconds were summed. As shown in FIG. 8, the summed current values were sufficient to distinguish between a control solution (that was substantially devoid of interferents) and blood samples.

In another embodiment, two characteristics of control solution are used to distinguish control solutions from blood—the presence and/or concentration of redox species in the sample and reaction kinetics. The method disclosed herein can include the step of calculating a first reference value that is representative of the redox concentration in the sample and a second reference value that is representative of the rate of reaction of the sample with the reagent. In one embodiment, the first reference value is an interferent oxidation current and the second reference value is a reaction completion percentage.

In regard to redox species in the sample, blood usually contains various endogenous redox species or "interferents" such as ascorbic acid and uric acid, as well as exogenously derived interferents such as gentisic acid (gentisic acid is a metabolite of aspirin). Endogenous interferents are chemical species that can be easily oxidized at an electrode and are usually present in blood within a physiological range for healthy individuals. Exogenously derived interferents are also a chemical species that can be easily oxidized at an electrode, but are not usually present in blood unless they are inputted into the body via consumption, injection, absorption, and the like.

Figure 9:
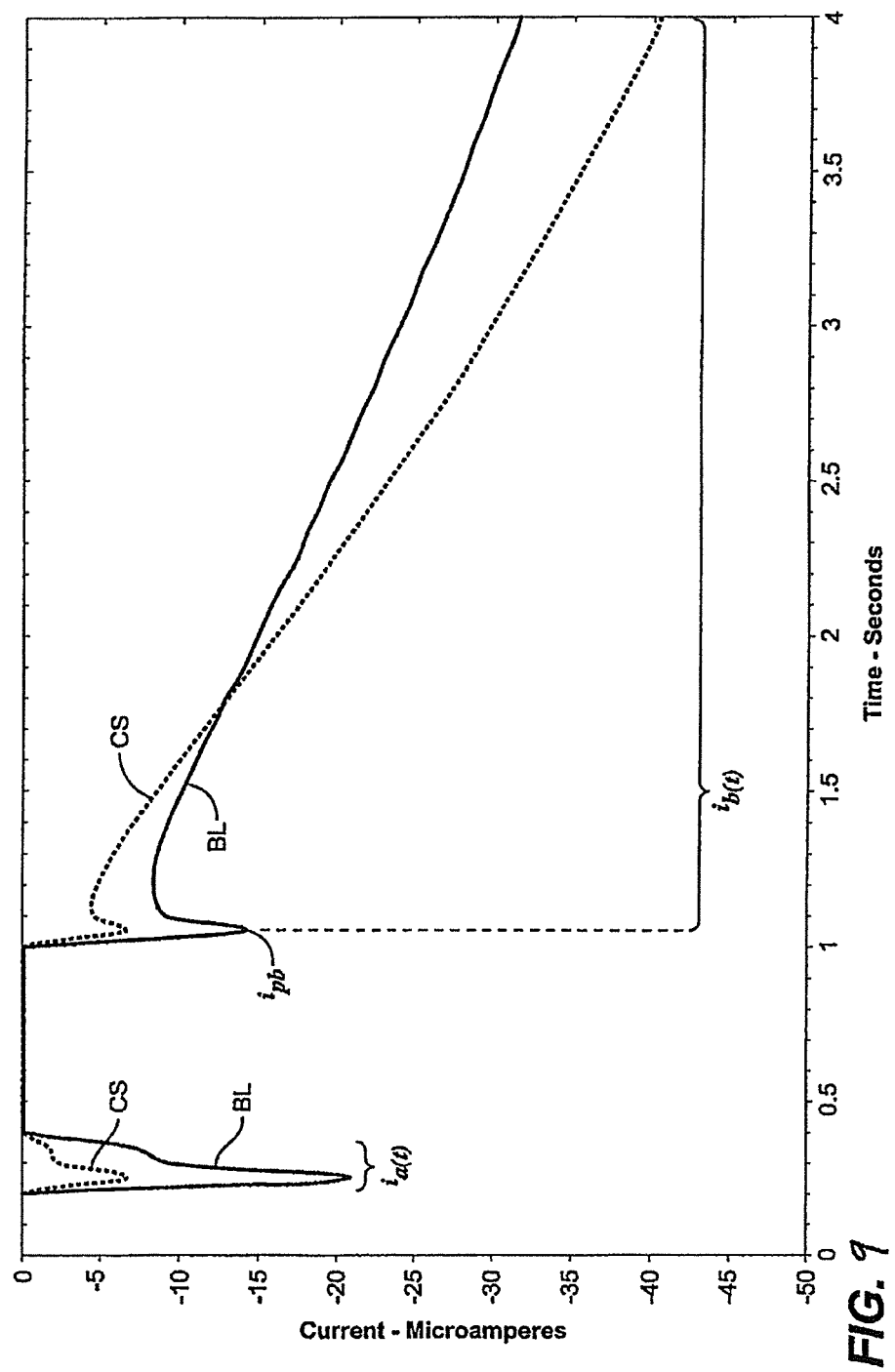
FIG. 9 is an expanded view of FIG. 7 showing a first test current transient and second test current transient for control solution (CS) and blood (BL)

A control solution can be formulated to be either essentially free of antioxidants or to have a relatively high interferent concentration compared to the interferent concentration in a blood sample. For the case in which the control solution is essentially free of antioxidants, the magnitude of the first current transient should be smaller for the control solution than for a blood sample as shown in FIG. 9. For the case in which control solution has a relatively high concentration of interferents, the magnitude of the first current transient should be larger for the control solution than for a blood sample (data not shown).

A first reference value can be calculated based on the current values within the first current transient. In one embodiment, the first reference value can include a summation of current values at two points in time during the first current transient. In one example, the current values at about 0.3 and about 0.35 seconds can be used when employing the test potential waveform of FIG. 6. In another embodiment when a test potential $E_1'$ is applied for the entire period between when fill is detected and the second test potential $E_2$, the first reference value is preferably obtained by summing two values over a longer period, for example about 0.2 seconds to about 0.5 seconds. In yet another embodiment, the first reference value can be obtained by a summation of the current values obtained during the first time current transient when using the test potential waveform of FIG. 12. As an example, the summation can be represented by Eq. 3:

$$i_{sum} = \sum_{t=0.05}^{1} i(t) \qquad \text{Eq. 3}$$

The terms $i_{sum}$ is the summation of current values and t is a time.

The first reference value can be referred to as an interferent index because it is proportional to the interferent concentration and should not substantially depend on the glucose concentration. Therefore, in theory, the test meter should be able to distinguish whether the sample is blood or control solution based on the interferent index. However, in practice, using only the interferent index did not always sufficiently discriminate between blood and the control solution. Although blood typically has a much higher interferent concentration, there are certain conditions in which the first current transient for blood may be attenuated such that it is comparable to control solution. These conditions include high glucose concentration, high hematocrit, low temperature, and incomplete filling of the sample reaction chamber 61. Thus, in one embodiment, an additional factor was implemented to enable the test meter to sufficiently discriminate between blood and control solution.

The additional factor used for helping discriminate between blood and control solution can be a second reference value. The second reference value may be referred to as a residual reaction index, which can be a value proportional to the percent of remaining substrate, which would have reacted if given enough time. The residual reaction index relates to the reaction rate in that a high reaction rate can cause the substrate to be depleted by the reaction. However, the residual reaction index will also depend on the initial magnitude of the substrate concentration.

The reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$, as shown in Eq. 4 below. Note that $GDH_{(ox)}$ refers to the oxidized state of GDH, and $GDH_{(red)}$ refers to the reduced state of GDH.

$$D\text{-Glucose} + GDH_{(ox)} \rightarrow \text{Gluconic acid} + GDH_{(red)} \quad \text{Eq. 4}$$

Next, $GDH_{(red)}$ is regenerated back to its active oxidized state by ferricyanide (i.e. oxidized mediator or $Fe(CN)_6^{3-}$) as shown in Eq. 5 below. In the process of regenerating $GDH_{(ox)}$, ferrocyanide (i.e. reduced mediator or $Fe(CN)_6^{4-}$) is generated from the reaction as shown in Eq. 5:

$$GDH_{(red)} + 2Fe(CN)_6^{3-} \rightarrow GDH_{(ox)} + 2Fe(CN)_6^{4-} \quad \text{Eq. 5}$$

In general, the rate of glucose consumption based on Eq. 4 and Eq. 5 is faster for control solution than for blood. Typically, the control solution is less viscous than blood causing the reaction rate of Eq. 4 and 5 to be faster for the control solution. Further, the reaction rate is faster for the control solution because a portion of the glucose present in the blood sample must diffuse out of the red blood cells to participate in Eq. 4. This extra step of glucose diffusion out of the red blood cells slows down the reaction rate to some measurable degree. FIG. 9 shows that the reaction rate for blood is slower than for control solution as evidenced by the fact that the general absolute slope value (e.g., between about 1.2 and about 4 seconds) for the second current transient is less for the blood sample. Because of the faster reaction rates in the control solution compared to blood, the residual reaction index for control solution will generally be lower than for blood.

The residual reaction index can be a number that is related to the percent of glucose that has not been consumed. In one embodiment, a relatively low residual reaction index can indicate that the reactions of Eq. 4 and Eq. 5 are close to completion. In contrast, a relatively high residual reaction index will indicate that the reaction is not close to completion. For example, the residual reaction index can be an absolute ratio of a current value of third current transient divided by a current value of the second current transient, as shown in Eq. 6:

$$\text{abs}\left(\frac{i(4.15)}{i(3.8)}\right) \quad \text{Eq. 6}$$

For the denominator of Eq. 6, the current value at 3.8 seconds for the second current transient was used. The time of 3.8 seconds was chosen empirically, however, one skilled in the art will appreciate that other current values can be used. In one embodiment, a current value at about the end of the second current transient is chosen. During the second test potential time interval $T_2$, the reduced mediator is oxidized at the second electrode 164. The magnitude of the current values measured during the second test potential time interval $T_2$ can be ascribed to the amount of ferrocyanide generated by the reagent layer 72 at the first electrode 166 and then diffused to the second electrode 164. It is assumed that reagent layer 72 remains close to first electrode 166 after it dissolves in blood. As a result, most of the ferrocyanide that is oxidized by second electrode 164 necessarily had to diffuse from the first electrode 166.

For the numerator of Eq. 6, the current value at 4.15 seconds was used. Other current values from the third current transient can be chosen, however the current value at about the beginning of the third current transient is preferred. During the third test potential time interval $T_3$, the reduced mediator is oxidized at first electrode 166. The magnitude of the current values measured during second test potential time interval $T_2$ can be ascribed to the amount of ferrocyanide generated by the reagent layer 72 at the first electrode 166 and did not diffuse sufficiently far away from the first electrode 166. As a result of the reagent layer 72 remaining close to the first electrode 166, the magnitude of the current values for the third current transient will be generally larger than the second current transient. In addition, third current transient will also be larger in magnitude than second current transient because the reagent layer 72 will have had more time to generate ferrocyanide. Thus, the absolute ratio as shown in Eq. 6 will be larger if the glucose reaction is still far from completion at the time of the measurement.

In another embodiment, a residual reaction index can be used, as shown in Eq. 7 below. The residual reaction index can increase to indicate that the reactions of Eq. 4 and Eq. 5 are closer to completion and decrease to indicate that the reactions are further from completion. It should be noted that Eq. 6 has a residual reaction index that ranges from about 1 to infinity and that Eq. 7 has a residual reaction index that ranges from about zero to about 1. Under certain circumstances, Eq. 7 may be a better discriminator for control solution than Eq. 6. For example, the residual reaction index can be an absolute ratio of a current value of the second current transient divided by a current value of the third current transient, as shown in Eq. 7:

$$\text{abs}\left(\frac{i(3.8)}{i(4.15)}\right) \quad \text{Eq. 7}$$

Figure 10:
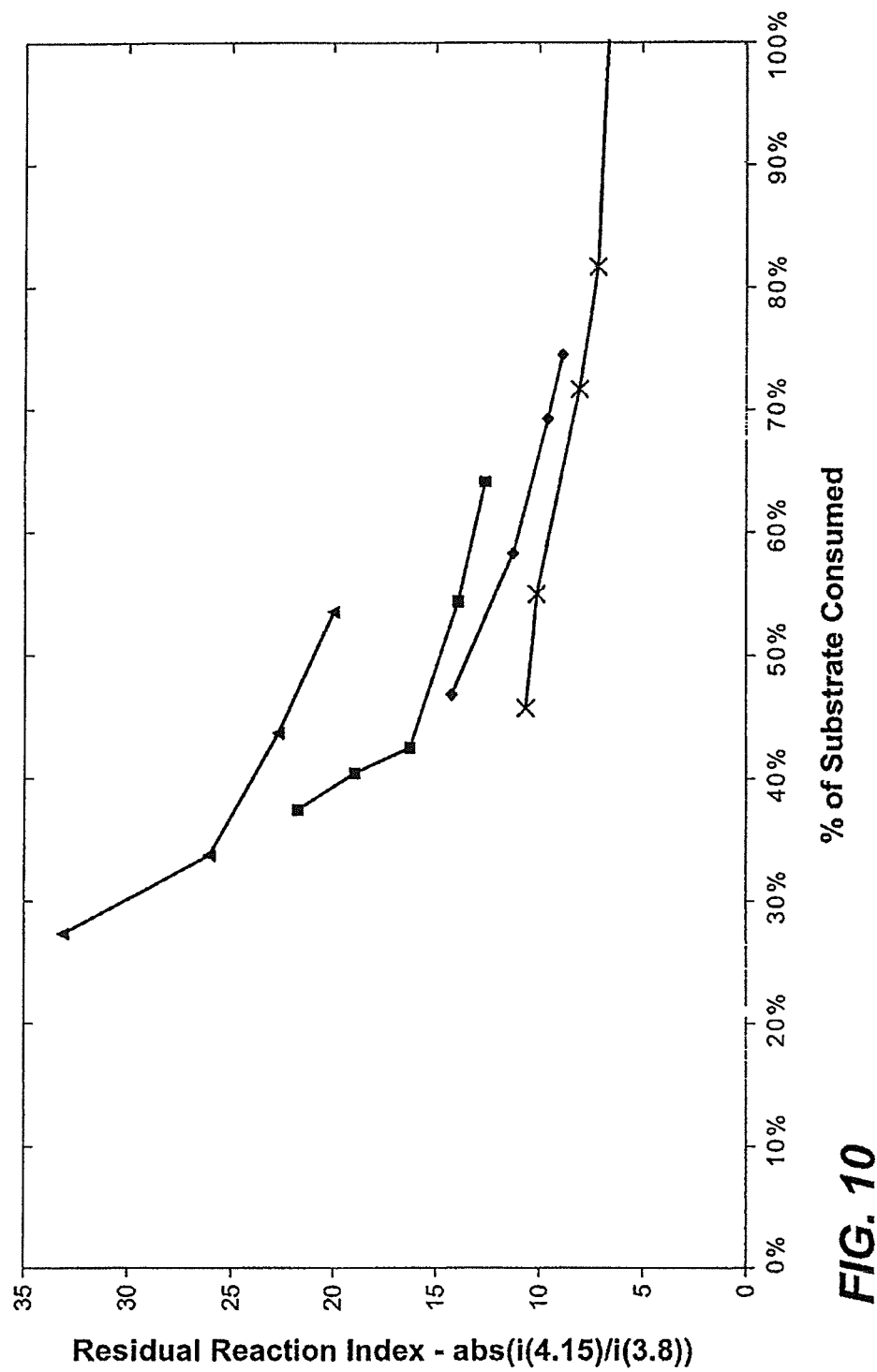
FIG. 10 is a chart showing a non-linear relationship between the percent of substrate consumed and the residual reaction index for blood samples having various hematocrit levels and for control solution (diamonds=25% hematocrit blood, squares=42% blood, triangles=60% hematocrit blood, x=control solution)

FIG. 10 is a chart showing a non-linear relationship between the estimated percent (%) of substrate consumed and the residual reaction index of Eq. 6 for blood samples having various hematocrit levels and for control solution (diamonds=25% hematocrit blood, squares=42% blood, triangles=60% hematocrit blood, x=control solution). FIG. 10 illustrates that the residual reaction index is relatively high when the % of substrate consumed is low and that the residual reaction index is relatively low when the % of substrate consumed is high for a given sample type/hematocrit value. The % of substrate consumed is estimated from a ratio $$\frac{C_o}{YSI},$$

where $C_o$ is an estimated substrate concentration at the electrode surface and YSI is the substrate concentration using a standard reference technique. The term $C_o$ is derived using the following Eq. 8.

$$C_o = \frac{i_{ss}L}{2FAD} \qquad \text{Eq. 8}$$

In this equation, L is the distance between the first electrode 166 and the second electrode 164, F is Faraday's constant, A is the area of the first electrode 166, and D is the diffusion coefficient. Further details regarding Eq. 8 can be found in U.S. Pat. No. 6,284,125, the entirety of which is hereby incorporated herein by reference.

Figure 11:
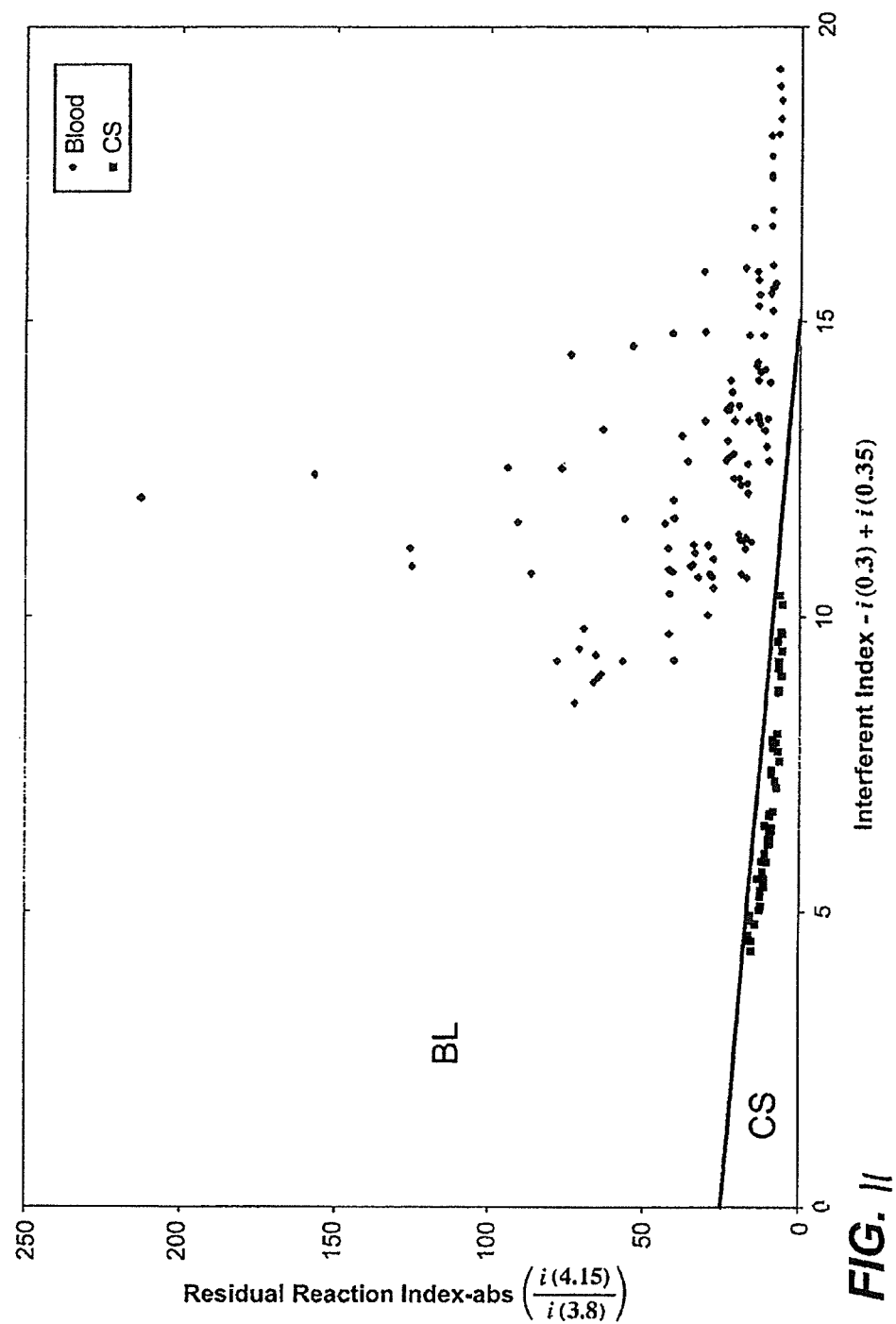
FIG. 11 is a chart showing a relationship between an interferent index and a residual reaction index for a plurality of blood samples (diamonds) and control solution samples (squares)

FIG. 11 is a chart showing a relationship between the interferent index and a residual reaction index for a plurality of blood samples and control solution samples. By plotting the interferent index on the X-axis and the residual reaction index on the Y-axis, a segregation between blood and control solution can be observed. A discrimination line can be drawn to determine if the sample is either a control solution or blood. In this embodiment, the interferent index is i(0.3)+i(0.35) and the residual reaction index is $$\text{abs}\left(\frac{i(4.15)}{i(3.8)}\right).$$

It should be noted that the times (e.g., 4.15, 3.8) at which the current values where selected for the residual reaction index, were found empirically. A large number of current ratios were evaluated for their ability to discriminate between blood and control solution samples. The ratio shown in either Eq. 6 or Eq. 7 was selected because it was found to produce significant separation between blood and control solution samples.

A discrimination line was derived to allow the test meter to determine whether the sample was control solution or blood. For all of the control solution samples tested, the interferent index was plotted versus the residual reaction index. Next, a line was calculated using linear regression for control solution samples. After calculating an equation for the line, the perpendicular bias between each data point and the line was calculated. The perpendicular bias represents the shortest distance between the data point and the line as opposed to a vertical bias that is commonly calculated. A standard deviation was determined for all of the perpendicular biases ($SD_{perp}$). Lastly, the line is shifted 3*$SD_{perp}$ units towards the data points for the blood group. The reason for this approach is that the data for the control solution group show very little scatter and therefore the "99% confidence limit" of the control solution group is well-defined.

In the method described herein, the information obtained from this statistical analysis of the residual reaction index and the interferent index can be used by the test meter to distinguish control solutions from blood samples. The test meter can calculate the interferent index and residual reaction index and use these values in association with the derived discrimination line (or an equation representing the discrimination line) to distinguish control solutions from blood samples.

Figure 14:
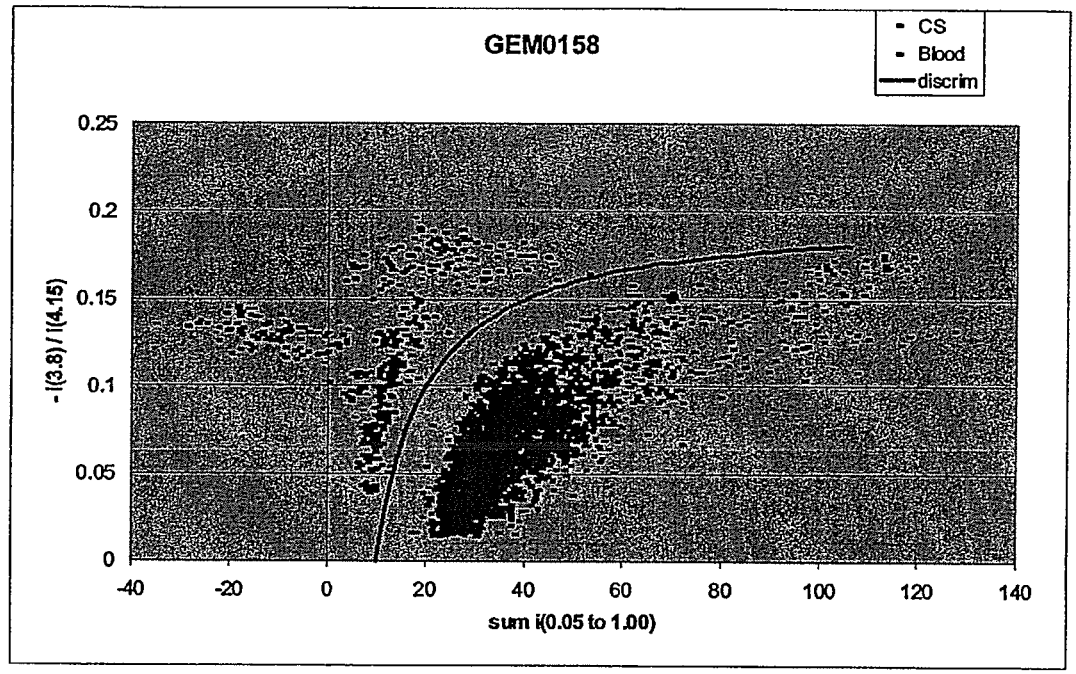
FIG. 14 is a chart showing a relationship between an interferent index and a residual reaction index using an alternative algorithm tested at a wide range of temperatures, hematocrit levels, and glucose concentrations.
Figure 15:
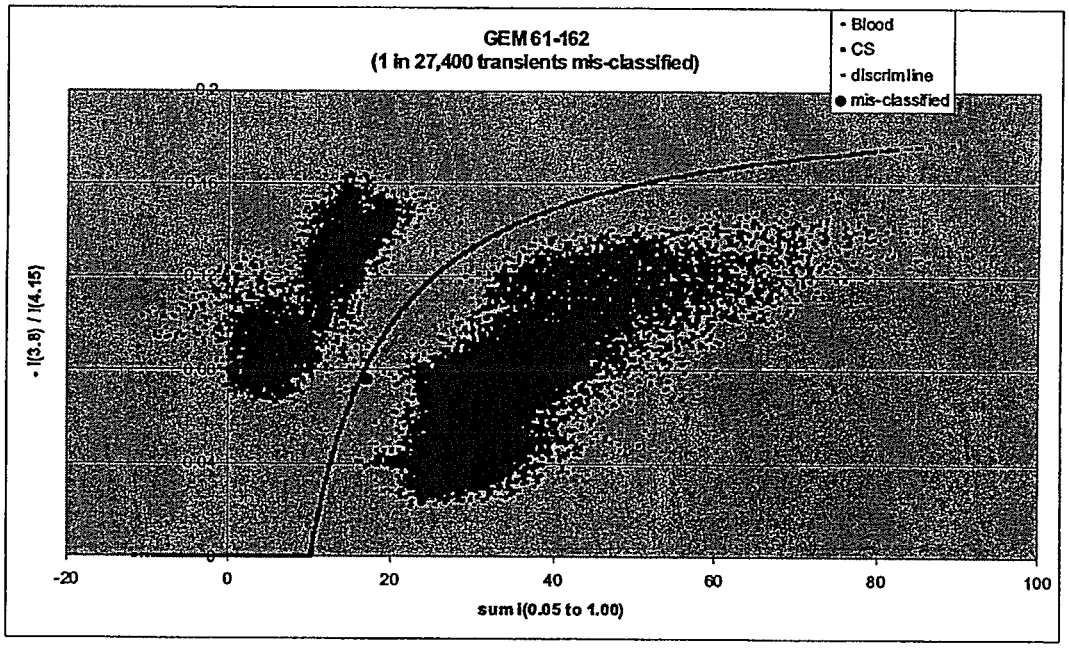
FIG. 15 is a chart showing a relationship between an interferent index and a residual reaction index using the alternative algorithm tested only at ambient temperature.

For the situation in which the test potential waveform of FIG. 12 is employed, an alternative algorithm for discriminating between control solution and blood may be used. The alternative algorithm includes using the interferent index of Eq. 3 and the residual reaction index of Eq. 7. FIG. 14 illustrates a chart showing the relationship between the interferent index and a residual reaction index for a plurality of blood samples and control solution samples using the alternative algorithm. In FIG. 14, blood samples and control solution samples were tested over a temperature range of about 5 degrees Celsius to about 45 degrees Celsius. Additionally, the blood samples had a glucose concentration range of about 20 mg/dL to about 560 mg/dL and a hematocrit level range of about 0% to about 60%. FIG. 15 illustrates another chart where more test strips (about 27,400) were tested using the alternative algorithm at room temperature only. By plotting the interferent index on the X-axis and the residual reaction index on the Y-axis, a segregation between blood and control solution can be observed in FIGS. 14 and 15.

A discrimination criteria can be used to determine if the sample is either control solution or blood based on the interferent index of Eq. 3 and the residual reaction index of Eq. 7. For example, the interferent index of Eq. 3 may be compared to a pre-determined threshold and the residual reaction index of Eq. 7 may be compared to a pre-determined threshold equation. The pre-determined threshold may be about 10 microamperes. The pre-determined threshold equation may be based on function using the interferent index. More specifically, the pre-determined threshold equation can be Eq. 9.

$$\text{abs}\left(\frac{i(3.8)}{i(4.15)}\right) < \frac{K*\left(\sum_{t=0.05}^{1} i(t)\right) - 10}{\sum_{t=0.05}^{1} i(t)} \qquad \text{Eq. 9}$$

The term K can be a constant such as, for example, about 0.2. Thus, the alternative algorithm can identify a sample as blood if $$\sum_{t=0.05}^{1} i(t) > 10 \text{ and if}$$

$$\text{abs}\left(\frac{i(3.8)}{i(4.15)}\right) < \frac{K*\left(\sum_{t=0.05}^{1} i(t)\right) - 10}{\sum_{t=0.05}^{1} i(t)},$$

else the sample is control solution.

EXAMPLES

Example 1

The following provides the preparation of the control solution which was utilized to generate the data of FIGS. 7 and 11.

This preparation is non-limiting as various other preparations and/or control solutions can be utilized with the currently disclosed system and method.

Citraconic acid Buffer Component 0.0833 g
Dipotassium citraconate Buffer Component 1.931 g
Methyl Paraben Preservative 0.050 g
Germal II Preservative 0.400 g
Dextran T-500 Viscosity Modifier 3.000 g
Pluronic 25R2 Wicking Agent 0.050 g
1-[(6-methoxy-4-sulfo-m-tolypazo]-2-naphthol-6-sulfonic acid disodium salt Dye (FD&C Blue No. 1) 0.100 g
D-Glucose Analyte 50, 120, or 525 mg
Deionized Water Solvent 100 g First citraconic buffer pH 6.5±0.1 was prepared by dissolving required quantities of citraconic acid and dipotassium citraconate in deionized water. Next, methyl paraben was added and the solution was stirred until the preservative was fully dissolved. Subsequently Dextran T-500, Germal II, Pluronic 25R2 and 1-[(6-methoxy-4-sulfo-m-tolyl)azo]-2-naphthol-6-sulfonic acid disodium salt were added sequentially, following complete dissolution of the previously added chemical. At this point, the pH of the control fluid was verified, followed by addition of the requisite quantity of glucose to obtain a low, normal or high glucose level of control fluid. After the glucose was dissolved completely, the control fluid was left at room temperature overnight. Finally, the glucose concentration was verified using a Model 2700 Select Biochemistry Analyzer manufactured by Yellow Springs Instrument Co., Inc. The dye used in this control solution has a blue color, which reduces the possibility of a user confusing control solution with blood.

Example 2

Some people (e.g., young people attempting to deceive parents or doctors) will load a sensor with Gatorade® as opposed to blood to give the impression that their glucose is under control. The following experiment was performed to determine if the currently disclosed method and sensor could be utilized to distinguish Gatorade® from blood.

Five (5) different flavors of Gatorade® were tested. The sensor classified all five flavors as a control solution (mean glucose=264 mg/dL; CV=6.7%). Thus, the sensor can be used to distinguish between Gatorade® and blood.

One skilled in the art will appreciate further features and advantages of the presently disclosed system and method based on the above-described embodiments. Accordingly, the presently disclosed system and method are not to be limited by what has been particularly shown and described, except as indicated by the appended claims. All publications and references cited herein are expressly incorporated herein by reference in their entirety.

What is claimed is:

1. A system for distinguishing between a blood sample and a control solution, the system comprising:
   (a) a test strip including electrical contacts for mating with a test meter and an electrochemical cell comprising;
      (i) a first electrode and a second electrode in a spaced apart relationship; and
      (ii) a reagent; and
   (b) a test meter including a processor programmed to measure and receive current data from the test strip, and data storage containing discrimination criteria for distinguishing a blood sample from a control solution, wherein the discrimination criteria is derived from an interferent index that is representative of antioxidant concentration and a residual reaction index that is representative of reaction kinetics between the reagent and an introduced liquid, in which the processor is programmed to calculate the interferent index based on a summation of current values measured during a first current transient and to determine the residual reaction index by calculating an absolute ratio involving current values obtained during second and third current transients,
   wherein the interferent index represents a first reference value and the residual reaction index represents a second reference value and in which the processor is further programmed to distinguish a blood sample from a control solution by comparing the calculated second reference value to a pre-determined threshold function based on the interferent index.

2. The system of claim 1, wherein the discrimination criteria includes an empirically derived discrimination line.

3. A system according to claim 1, wherein the introduced liquid is a control solution if the second reference value is less than the following pre-determined threshold function:

$$\frac{K * \left( \sum_{t=0.05}^{1} i(t) \right) - 10}{\sum_{t=0.05}^{1} i(t)}$$

in which K is a constant.

4. A system according to claim 1, in which the processor is programmed to compare the calculated first reference value to a pre-determined threshold and then depending on the results of the first reference value comparison, the processor is further programmed to calculate the second reference value and compare the calculated second reference value to the pre-determined threshold function.

5. A system according to claim 4, wherein the pre-determined threshold is about 10 microamperes.

* * * * *